(12) United States Patent
Faubert et al.

(10) Patent No.: US 10,441,207 B2
(45) Date of Patent: Oct. 15, 2019

(54) CONFIGURABLE SYSTEM FOR EVALUATING STIMULUS SENSITIVITY OF A SUBJECT AND METHOD OF USE THEREFOR

(71) Applicants: Jocelyn Faubert, Montrèal (CA); Rafael Doti, Montrèal (CA); Jesus-Eduardo Lugo-Arce, Laval (CA)

(72) Inventors: Jocelyn Faubert, Montrèal (CA); Rafael Doti, Montrèal (CA); Jesus-Eduardo Lugo-Arce, Laval (CA)

(73) Assignee: COGNISENS INC., Montreal QC (CA)

( * ) Notice: Subject to any disclaimer, the term of this patent is extended or adjusted under 35 U.S.C. 154(b) by 0 days.

(21) Appl. No.: 15/302,920

(22) PCT Filed: Apr. 2, 2015

(86) PCT No.: PCT/CA2015/050274
§ 371 (c)(1),
(2) Date: Oct. 7, 2016

(87) PCT Pub. No.: WO2015/154178
PCT Pub. Date: Oct. 15, 2015

(65) Prior Publication Data
US 2017/0035339 A1    Feb. 9, 2017

Related U.S. Application Data

(60) Provisional application No. 61/976,002, filed on Apr. 7, 2014.

(51) Int. Cl.
*A61B 5/00* (2006.01)
*A61B 5/16* (2006.01)
(Continued)

(52) U.S. Cl.
CPC .............. *A61B 5/162* (2013.01); *A61B 3/02* (2013.01); *A61B 5/0051* (2013.01);
(Continued)

(58) Field of Classification Search
CPC ........... A61B 3/02; A61B 5/0051; A61B 5/01; A61B 5/1124; A61B 5/123; A61B 5/125;
(Continued)

(56) References Cited

U.S. PATENT DOCUMENTS

| | | | |
|---|---|---|---|
| 2006/0161218 A1* | 7/2006 | Danilov | A61B 5/0492 607/45 |
| 2011/0005532 A1* | 1/2011 | Faubert | A61M 21/00 128/898 |

FOREIGN PATENT DOCUMENTS

| | | |
|---|---|---|
| AU | 2014200477 A1 | 2/2014 |
| CA | 2 697 997 A1 | 4/2008 |
| WO | WO 2013/015730 A1 | 1/2013 |

OTHER PUBLICATIONS

Lugo, et al., "Ubiquitous Crossmodal Stochastic Resonance in Humans: Auditory Noise Facilitates Tactile, Visual and Proprioceptive Sensations," PLoS ONE, Aug. 2008, vol. 3, Issue 8, e2860.
(Continued)

*Primary Examiner* — George Manuel
(74) *Attorney, Agent, or Firm* — Praxis

(57) ABSTRACT

A configurable system is used to evaluate stimulus sensitivity of a subject. An action channel provides a stimulus to the subject and a reaction channel receives a response from the subject. A signal pathway is connected to the action channel and to the reaction channel. A controller establishes loops within the signal pathway. Loop types include a transduction loop including the action channel and forming a path terminating in the signal pathway, and a channel loop including the action channel and terminating at a reference unit. Other possible loop types include an interface loop including the
(Continued)

action channel, the reaction channel and the reference unit having an initial parameter value, and an adaptive loop including the action channel, the reaction channel and the reference unit whose parameter value is adapted based on the response from the subject. A method using the system is also described.

24 Claims, 26 Drawing Sheets

(51) Int. Cl.
    *A61B 5/11* (2006.01)
    *A61B 5/12* (2006.01)
    *A61B 3/02* (2006.01)
    *A61B 5/01* (2006.01)

(52) U.S. Cl.
    CPC ............ *A61B 5/1124* (2013.01); *A61B 5/123* (2013.01); *A61B 5/125* (2013.01); *A61B 5/4005* (2013.01); *A61B 5/4011* (2013.01); *A61B 5/4017* (2013.01); *A61B 5/483* (2013.01); *A61B 5/486* (2013.01); *A61B 5/7225* (2013.01); *A61B 5/7455* (2013.01); *A61B 5/01* (2013.01); *A61B 2560/0223* (2013.01)

(58) Field of Classification Search
    CPC ..... A61B 5/162; A61B 5/4005; A61B 5/4011; A61B 5/4017; A61B 5/483; A61B 5/7455; A61B 2560/0223; A61B 5/486; A61B 5/7225

See application file for complete search history.

(56) References Cited

OTHER PUBLICATIONS

Lugo, et al., "The Impact of Stochastic and Deterministic Sounds on Visual, Tactile and Proprioceptive Modalities", Advances in Sound Localization, Chapter 23, Apr. 11, 2011, ISBN 978-953-307-224-1, DOI: 10.5772/597.

Lugo, et al., "On the Physical Fundamentals of Human Perception and Muscle Dynamics: From the Fulcrum Principle to Phonons", 11th International Conference on Vibration Problems, Lisbon, Portugal, Sep. 9-12, 2013.

West et al., "Stochastic Resonance in Human Cognition: ACT-R Versus Game Theory, Associative Neural Networks, Recursive Neural Networks, Q-Learning, and Humans", 27th Annual Meeting of the Cognitive Science Society, Jul. 21-23, 2005, Stresa, Italy.

\* cited by examiner

CONFIGURABLE SYSTEM FOR EVALUATING STIMULUS SENSITIVITY OF A SUBJECT AND METHOD OF USE THEREFOR

TECHNICAL FIELD

The present disclosure generally relates to perceived reality enhancement and perception improvement. More specifically, but not exclusively, the present disclosure is concerned with a configurable system for evaluating stimulus sensitivity of a subject and with a method of use therefor.

BACKGROUND

The Fulcrum Principle is a phenomenon that occurs in different human systems. The Fulcrum Principle allows for improving the detectability of a signal below a threshold by injecting either a stochastic or a deterministic signal into the systems. Therefore, the Fulcrum Principle appears to be an interesting and attractive phenomenon to be applied in sensory systems in order to improve the sensitivity of the subject's sensory, reflex and/or motor mechanisms. A discussion of the Fulcrum Principle may be found in "On The Physical Fundamentals Of Human Perception And Muscle Dynamics: From The Fulcrum Principle To Phonons", J. E. Lugo et al., 11$^{th}$ International Conference on Vibration Problems, Z. Dimitrovová et al. (editors), Lisbon, Portugal, 9-12 Sep. 2013, the disclosure of which being incorporated by reference herein in its entirety.

Indeed, it has been shown that, when a weak sensory stimulus (excitatory signal) applied to an individual, for stimulating one sensory, reflex and/or motor mechanisms, is added to a second sensory, reflex and/or motor mechanisms with an appropriate amount of stochastic or deterministic signal amplitude (facilitation signal), the weak sensory stimulus can then be detected and thus activate the reactions of that particular sensory, reflex and/or motor mechanisms in response to the applied weak sensory stimulus.

For example, US Patent Publication no 2011/0005532 A1, entitled "Method and System for Improving a Subject's Sensory, Reflex and/or Motor Mechanisms via Auditory, Tactile or Visual Stimulations", the disclosure of which being incorporated by reference herein in its entirety, describes a method and a system for improving sensitivity of a first sensory, reflex and/or motor mechanism of a subject by stimulating a second sensory, reflex and/or motor mechanism of the subject. For that purpose a noise is applied to the second sensory, reflex and/or motor mechanism to improve the sensitivity of the first sensory, reflex and/or motor mechanism due to cross-modal stochastic resonance interactions.

There remains a need to improve definition, control and flexibility of stimulation applied at a second sensory, reflex and/or motor mechanism of the subject.

SUMMARY

According to the present disclosure, there is provided a system for evaluating stimulus sensitivity of a subject. In the system, a first action channel is configured to provide a first type stimulus to the subject. A reaction channel is configured to receive a response from the subject. A signal pathway is connected to the first action channel and to the reaction channel. A controller is adapted to establish at least one of a first transduction loop including the first action channel and forming a path terminating in the signal pathway, and a first channel loop including the first action channel forming a path through the signal pathway and terminating at a first reference unit.

According to the present disclosure, there is also provided a method for or evaluating stimulus sensitivity of a subject. The method uses a system for evaluating stimulus sensitivity of a subject. In the system, a first action channel is configured to provide a first type stimulus to the subject. A reaction channel is configured to receive a response from the subject. A signal pathway is connected to the first action channel and to the reaction channel. A controller is adapted to establish at least one of a first transduction loop including the first action channel and forming a path terminating in the signal pathway, and a first channel loop including the first action channel forming a path through the signal pathway and terminating at a first reference unit. The first action channel is used as a source of an excitatory signal to stimulate a first sensory, reflex and/or motor mechanism of the subject. The second action channel is used as a source of a facilitation signal to stimulate a second sensory, reflex and/or motor mechanism of the subject. The reaction channel is used to measure a physiological response of the first sensory, reflex and/or motor mechanism.

According to the present disclosure, there is also provided a system for improving sensitivity of a first sensory, reflex and/or motor mechanism of a subject. In the system, a source of a facilitation signal stimulates a second sensory, reflex and/or motor mechanism of the subject. A measures a physiological response of the first sensory, reflex and/or motor mechanism. A controller adjusts a level of the facilitation signal based on the measured physiological response. Adjusting the level of the facilitation signal improves the sensitivity of the first sensory, reflex and/or motor mechanism of a subject due to Fulcrum Principle interactions.

The foregoing and other features will become more apparent upon reading of the following non-restrictive description of illustrative embodiments thereof, given by way of example only with reference to the accompanying drawings.

BRIEF DESCRIPTION OF THE DRAWINGS

Embodiments of the disclosure will be described by way of example only with reference to the accompanying drawings, in which.

Like numerals represent like features on the various drawings.

DETAILED DESCRIPTION

A system disclosed herein allows exploring perceived sensations limits of a subject under test, while conditioning improving, learning, and/or letting acquire enhanced abilities and control of the subject senses perception. The system uses various types of stimulus loops, including combined, single pass amplified, feedback, feedforward, adaptive-feedback or bio-feedback stimulus loops. Additionally, the present disclosure provides a method and system for improving a subject's sensory, reflex and/or motor mechanisms via sensory stimulations by means of a stimulus loop configurable interface. Stimulus loops may be open or closed automatically via stochastic or deterministic signals to stabilize and maintain a subject on an optimal performance state.

Accordingly, a configurable interface allows an automatic selection of a variety of experimental configurations. The interface supports several configuration types defined by the stimulus loops that are desired for experiment to be performed.

Figure 1:
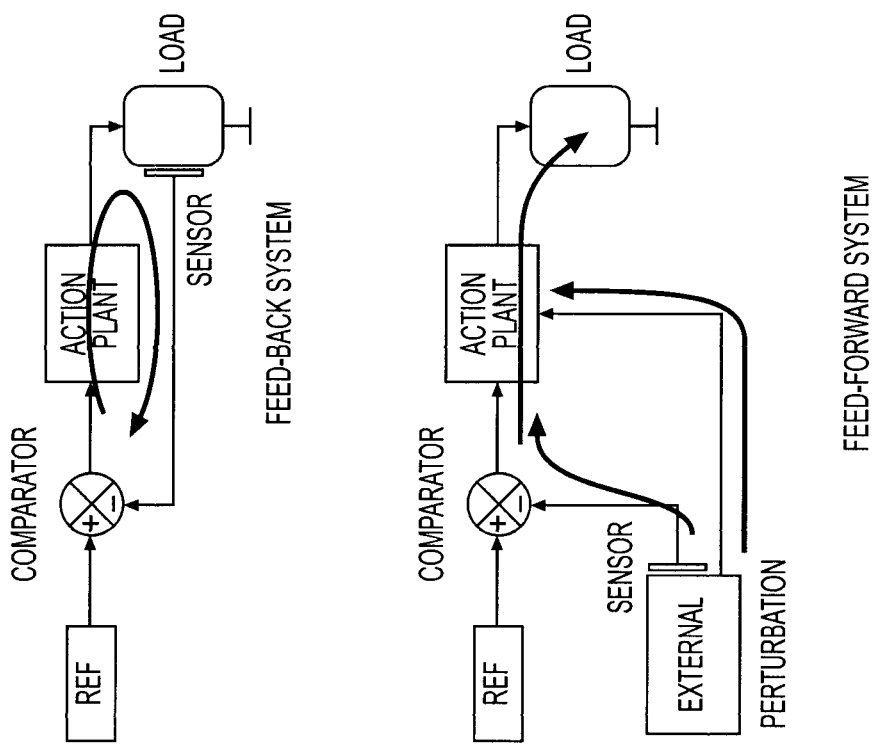
FIG. 1 shows simplified block diagrams of a feedback system and of a feedforward system.

Referring now to the drawings, FIG. 1 shows simplified block diagrams of a feedback system and of a feedforward system. Stimulus loops may be defined as a function of a stimulus to be applied and as a function of a specific effect in the subject's perception or training. The loops, feedback stabilization action between specific points, with or without feedforward compensation, may also be defined at different block levels, including activators level, channel level, involving several channels, or involving the subject himself. Loops may be implemented involving analog signals, digital signals or a mix thereof, applying converters when needed.

The loops may be defined as real time loops (RTL), delayed time loops (DL) where a loop gain presents a delay, delay compensated loops (DCL) that compensate a time needed for signal processing to apply several stimuli simultaneously, cadence Loops (CL) in which the loop action is delayed in a pre-established, random or sequential manner, and the like. The delay is inside of the amplifier or an additional specific block (not shown). The main function of the delay is to compensate the difference between propagation times on the channels. All loops defined herein may have a delay.

Close loops configurations allow to stabilize relationships between parameters of an electric circuit according to a sampled variable and a feedback variable. The sampled and feedback variables may for instance be current or voltage values. A stabilized rate, for instance a voltage gain, is used as a reference to two specific points in which a signal is first assessed and then reintroduced topologically in the circuit, thus closing the loop. If it is desired to add closed loop feedback stabilization into a specific stimulus channel, as a typical example of negative feedback, an evaluation of an output signal from the channel action is made at a first point of the two points, using a sensor. An electric network sensor, a microphone, a thermometer, or any other similar sensor may be used. The sensor feeds a fraction of the assessed output signal into a feedback amplifier of a feedback pass. Generally, but not exclusively, the feedback amplifier will have a gain of less than unity. An output of the feedback amplifier is subtracted from a reference signal at a second point, at the input of an action amplifier in a direct pass.

Many standard sensors are scalar sensors. Use of vector sensors, whose output not only depends on magnitude values but also on the sensor alignment into space, is also contemplated.

In the feedforward case, the system has a predetermined behavior in front of environmental perturbations.

Figure 2:
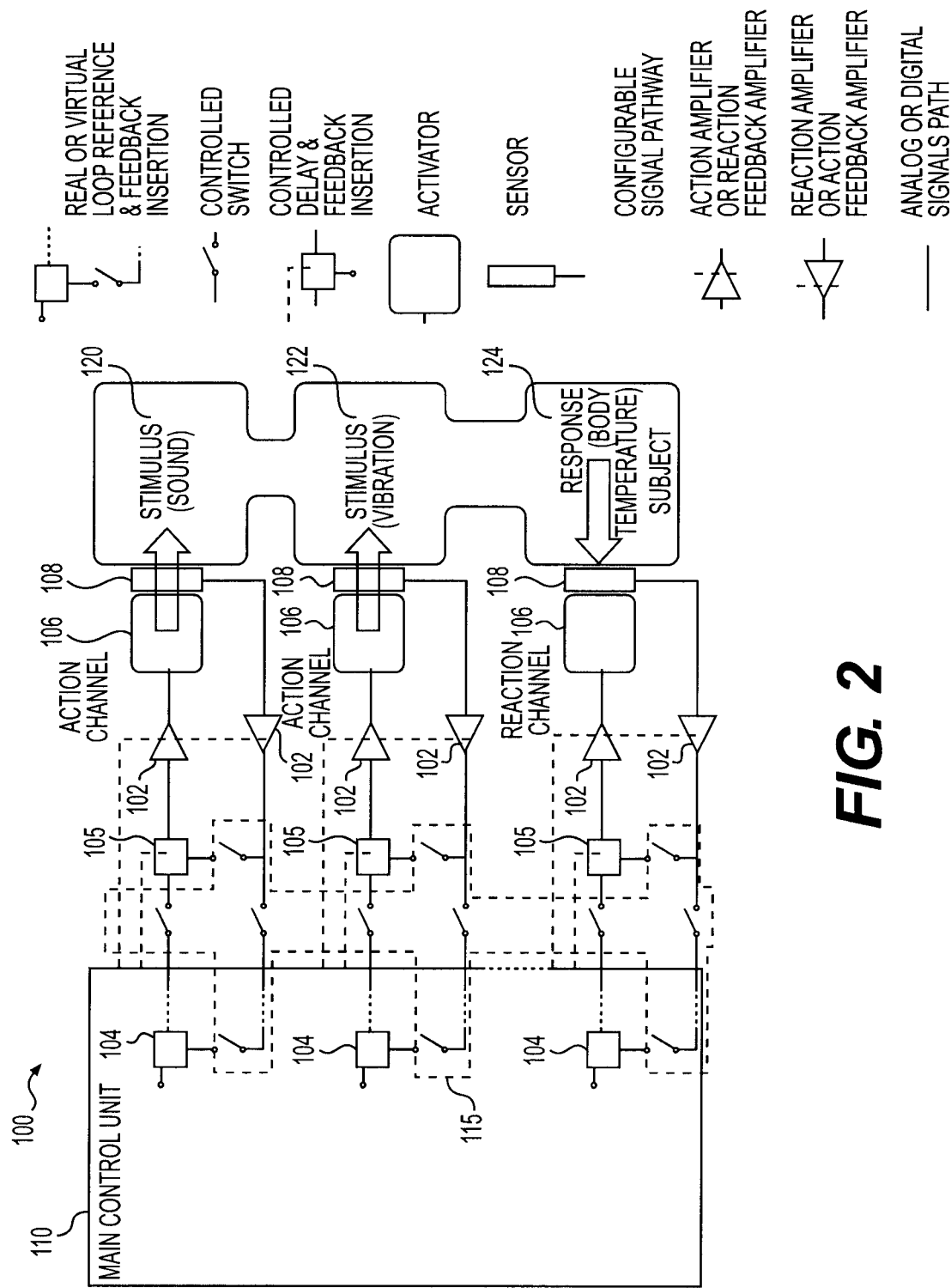
FIG. 2 is a block diagram illustrating a system for stimulating a subject according to an embodiment.

FIG. 2 is a block diagram illustrating a system for stimulating a subject according to an embodiment. The system 100 comprises an arrangement of control devices 104, 105, amplifiers 102, actuators 106, sensors 108, power supply (shown on later Figures), operator interface (shown on later Figures), and an active signal manager device in a main control unit 110, arranged to accomplish tasks related to evaluating stimulus sensitivity of a subject. FIG. 2 provides a non-limiting example of the system 100 having two (2) action channels and one (1) reaction channel, each action and reaction channel including one actuator 106 and one sensor 108. Actual numbers of action channels and reaction channels may vary and there is no a priori limit to these numbers. Each of these channels is configurable to provide a direct (forward) pass and a feedback (reverse) pass, as described in more details herein below. The main control unit 110 operates switches (described hereinbelow) that open and close to configure a configurable signal pathway 115. The configurable signal pathway 115 extends from the main control unit 110 itself to connect the main control unit to the action channels and to reaction channels. The control devices 104 and 105 may be implemented in the form of relays. Those relays 105 that are external to the main control unit 110 are generally implemented as actual physical devices (real relays). Those relays 104 that are integral to the main control unit 110 may either be implemented as actual physical devices or by software (virtual relays).

Action channels manage system actions on the subject. In the example of FIG. 2, the two (2) action channels provide an auditory stimulus 120 and a tactile stimulus (vibration) 122 to a subject under test. These action channels may be open loop channels. Alternatively, the action channels may be feedback channels realized at a channel level or at a transduction level. As a signal flows from the main control unit 110 to the subject, in the case of negative feedback, a gain on a direct pass represented by an amplifier 102 (triangle aimed to the right) is negative and has a magnitude greater than one. Therefore the gain in a feedback pass represented by an amplifier 102 (triangle aimed to the left) has a positive value, less than unity.

Reaction channels manage subject actions (i.e. reactions) on the system 100. The reaction channel allows a signal to flow from the subject to the main control unit 110. In the example of FIG. 2, the reaction channel measures a body temperature 124, which is provided in signal form to the main control unit 110. In the case of the reaction channel, for a negative feedback, the direct pass is from the reaction channel to the main control unit 110 and has a negative gain greater than one while the feedback pass is in the opposite direction, having a positive gain less than unity.

For the action channels, the sensors 108 evaluate the evolution of the output signals applied to the subject. The activators 106 of the action channels provide these signals to the subject. Corresponding sensors 108 supervise the activators 106 performance. For the reaction channels instead, the sensors 108 provide signals representing responses of the subject, for example a body temperature, and the activators 106 represents the feedback compensation for these sensors 108 to control their efficiency in the transduction of the subject reactions in terms of temperature, force, skin resistivity, and the like. Action channel and reaction channel configurations need not be implemented with electronic circuits. In the case of mass transferred equipment (e.g. fluid heaters or liquid coolers), mechanical actuators and electromagnetic devices, pneumatic interfaces (e.g. to measure blood pressure) may need regulator actions, or valves. These are examples of activators in the reaction channel.

It may be observed that the configurable signal pathway 115 formed by switches SW1, SW2, SW3 and SW4 that open and close per commands from the control devices 104 and 105 allows reconfiguring the system 100 of FIG. 2 so that an action channel may become a reaction channel, possibly presenting positive or negative feedback or feedforward. This dynamic configuration is configurable according a pre-established program or, alternatively, according to the subject responses. Reconfiguration may be done in real or delayed time. The system 100 may allow a practitioner to seek the subject's responses within an ongoing test, adopting the most efficient configuration appropriate for ongoing test conditions.

Figure 3:
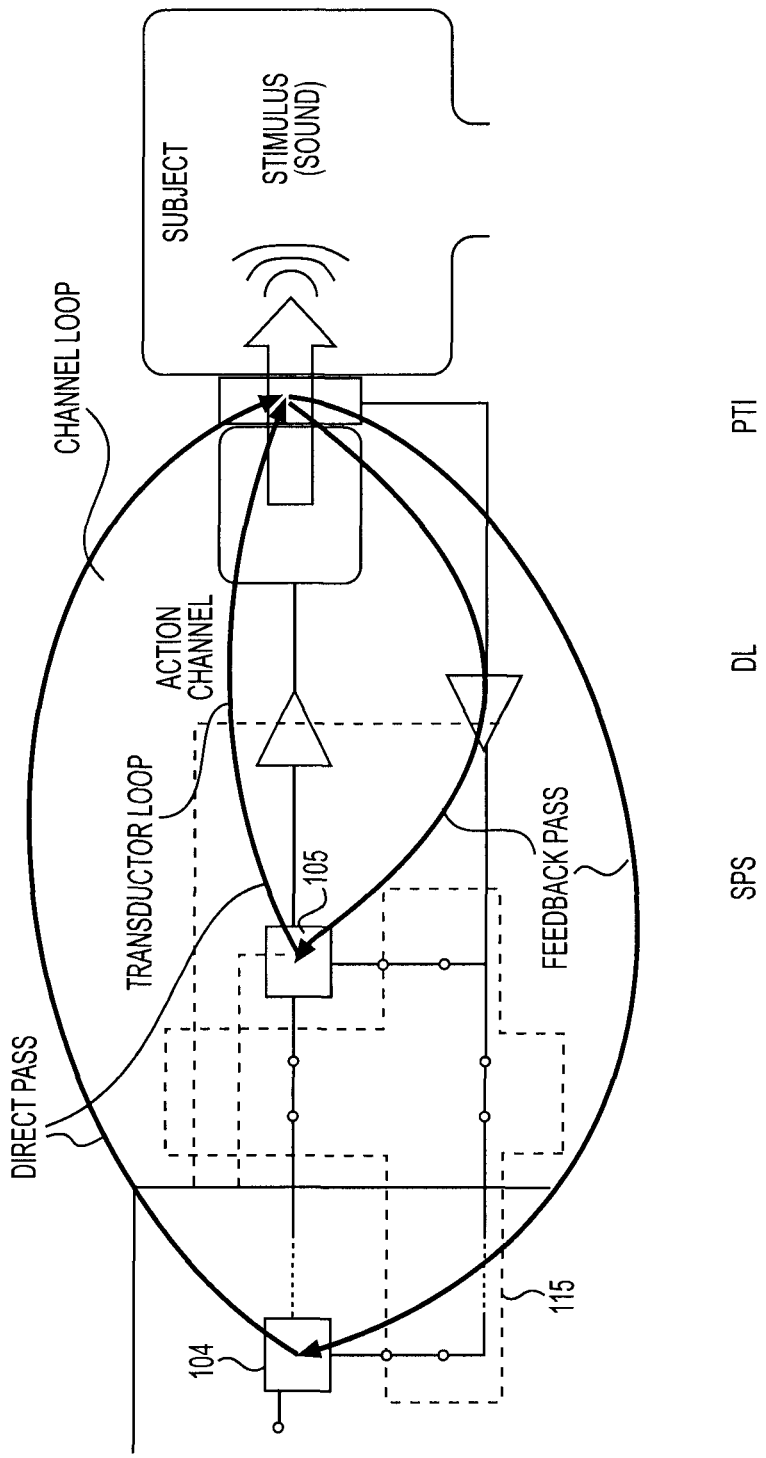
FIG. 3 is an example of a single point stimulus, direct loop, configured in pure trans-immitance in the system of FIG. 2.
Figure 4:
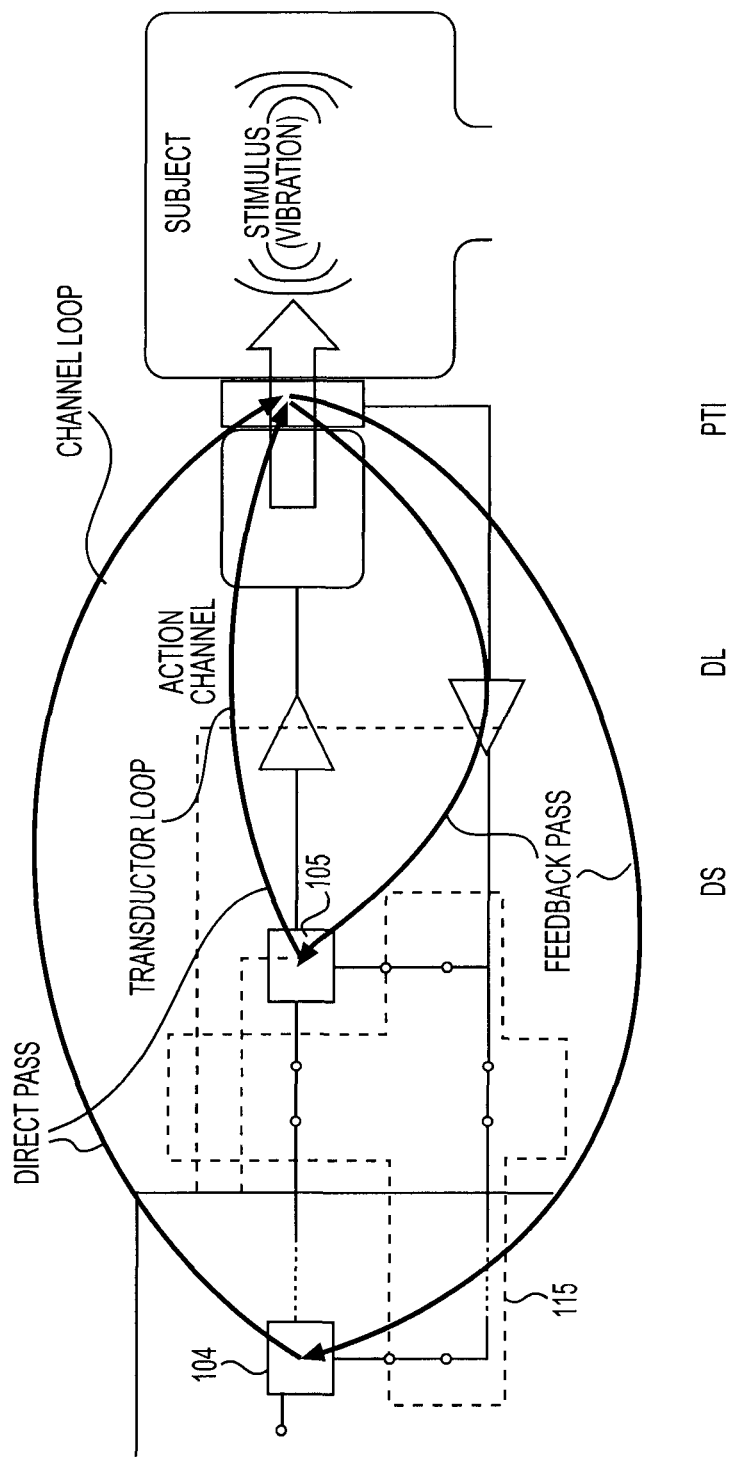
FIG. 4 is an example of a distributed stimulus, direct loop, configured in pure trans-immitance in the system of FIG. 2.

FIG. 3 is an example of a single point stimulus, direct loop, configured in pure trans-immitance in the system of FIG. 2. Loops as those shown on FIG. 3 provide single point stimuli (SPS). One example shown on FIG. 3 is a sound stimulus. Another type of SPS is a point light source. FIG. 4 is an example of a distributed stimulus, direct loop, configured in pure trans-immitance in the system of FIG. 2. A distributed stimulus may be provided using one or more activators. For example, a vibration stimulus can be provided using a single wide surface activator, as in the case of FIG. 4. Alternatively, a plurality of single point activators may be used. Loops as those shown on FIG. 4 provide distributed stimuli (DS). FIG. 4 shows an example in which vibrating surfaces are attached to the subject's body. In both FIGS. 3 and 4, illustrated loops are direct loops (DL) that unimodal interactions acting in pure trans-immitance (PTI), on a single sense of the subject, using for example a vibrating pin acting on a finger or a vibrating surface acting on the whole hand palm.

Figure 5:
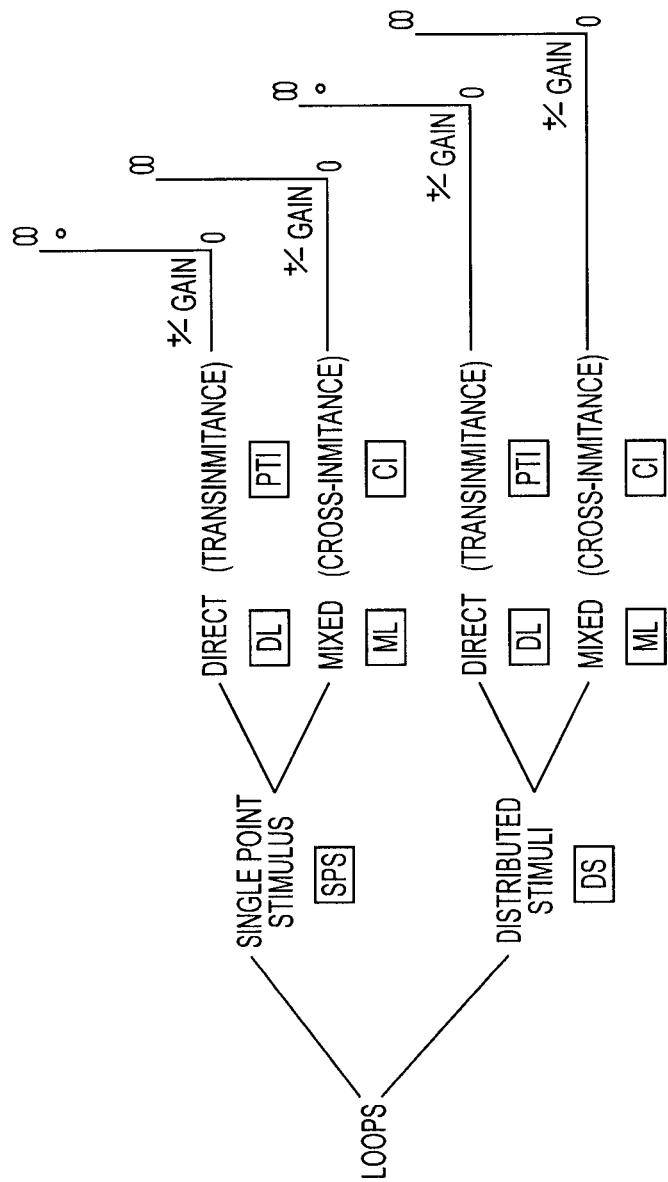
FIG. 5 is a tree diagram showing a loop classification of the present disclosure.

FIG. 5 is a tree diagram showing a loop classification of the present disclosure. Loops may comprise single point stimuli (SPS) or distributed stimuli (DS), as introduced hereinabove. Either may be provided as direct loops (DL) or as mixed loop (ML), in which a single or a distributed stimulus acts on a combination of senses, for example by providing audio and video stimuli simultaneously. ML examples are provided herein below. Distributed stimuli are provided in pure trans-immitance (PTI) while mixed stimuli are provided in cross-immitance (CI). PTI examples are provided in FIGS. 3 and 4 while CI examples are provided herein below. Each given loop may have a positive or a negative gain, with a gain magnitude in a range from zero (0) to infinity ($\infty$).

Figure 6:
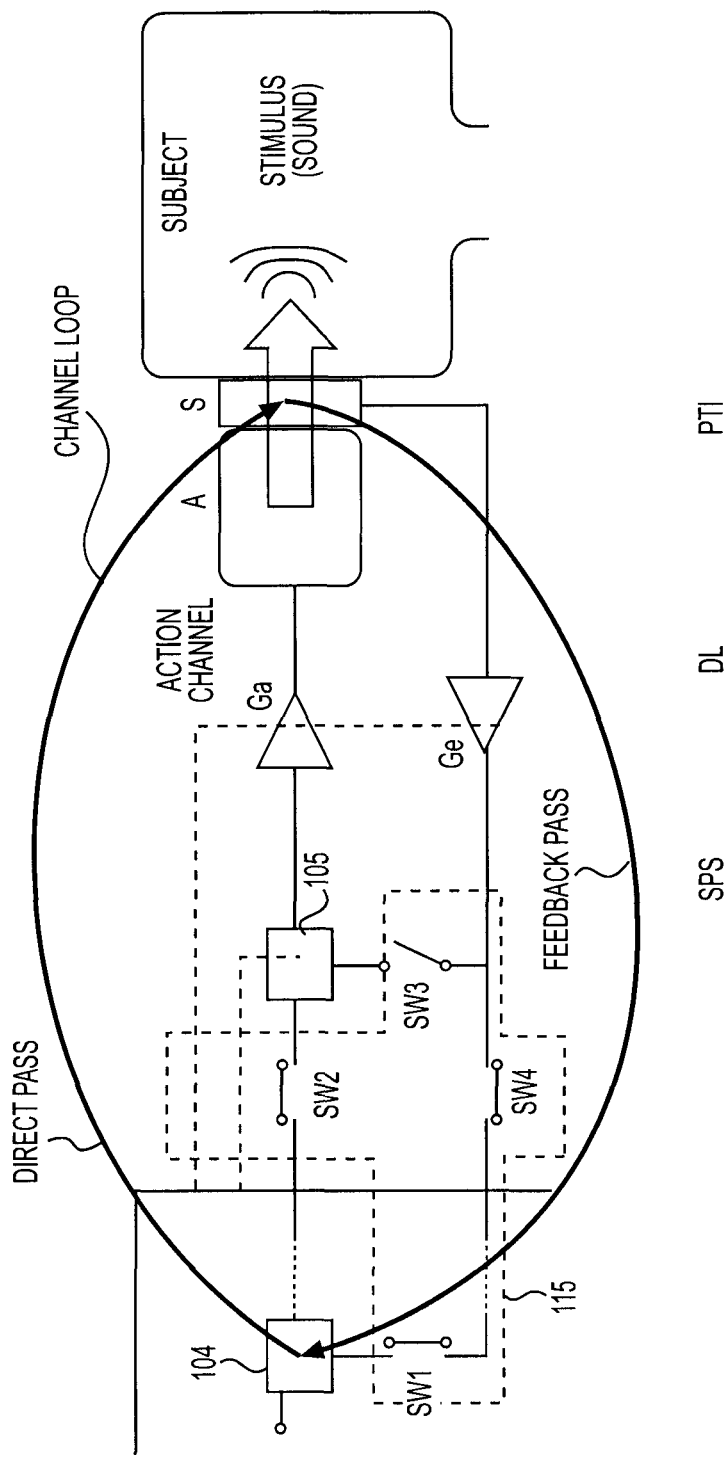
FIG. 6 is a configuration of the system of FIG. 2 showing switch positions for a channel loop for a single point stimulus.
Figure 7:
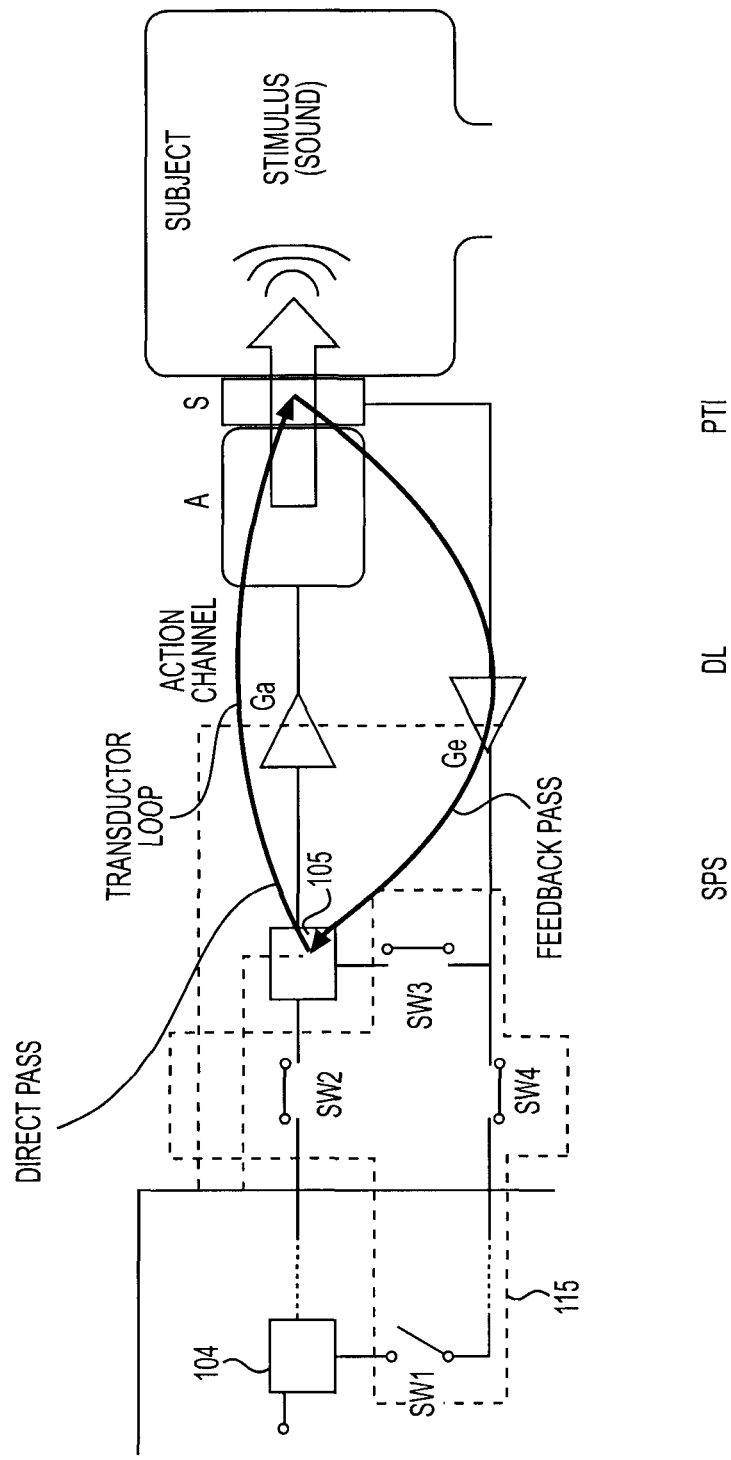
FIG. 7 is a configuration of the system of FIG. 2 showing switch positions for a transducer loop for a single point stimulus.
Figure 8:
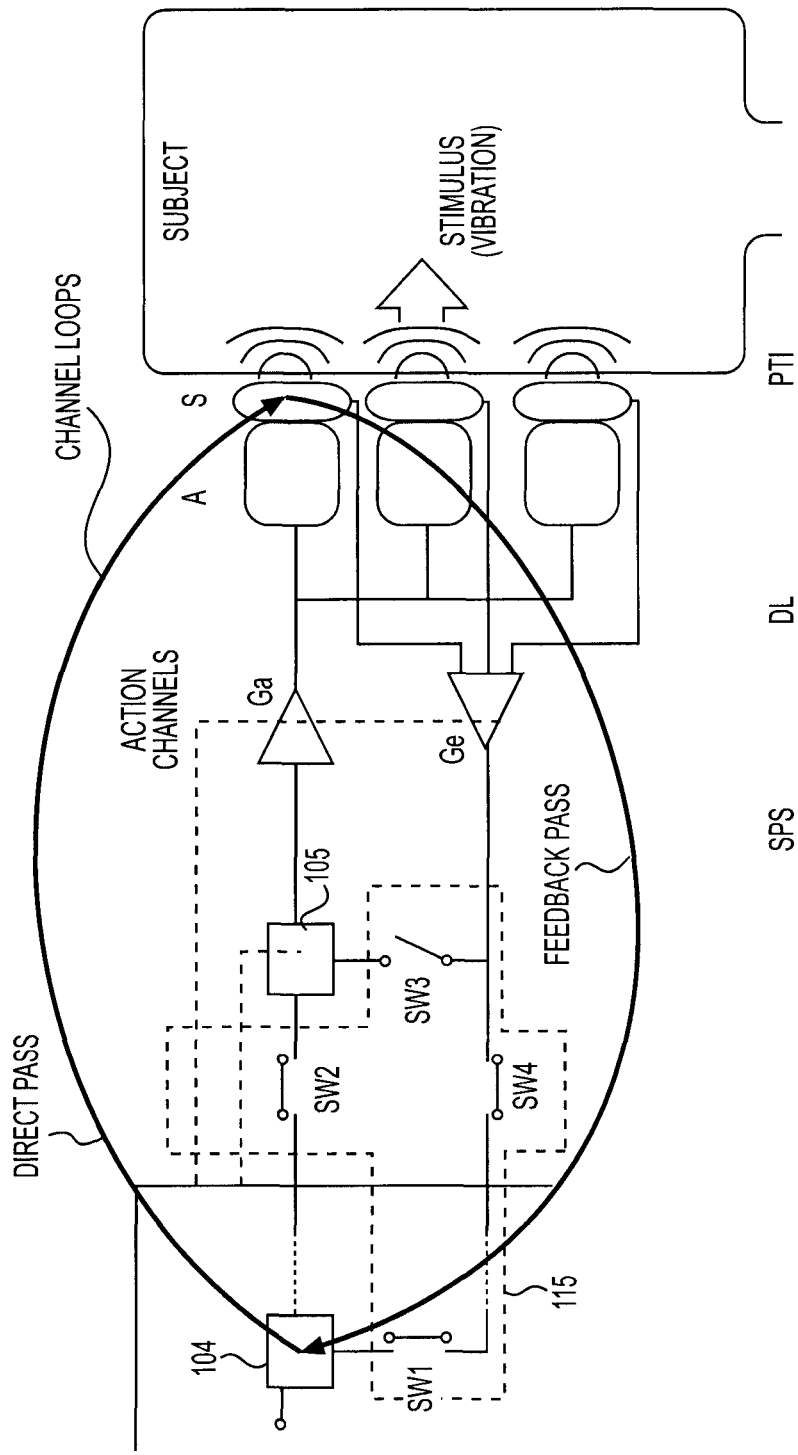
FIG. 8 is a configuration of the system of FIG. 2 showing switch positions for a channel loop for a distributed stimulus.
Figure 9:
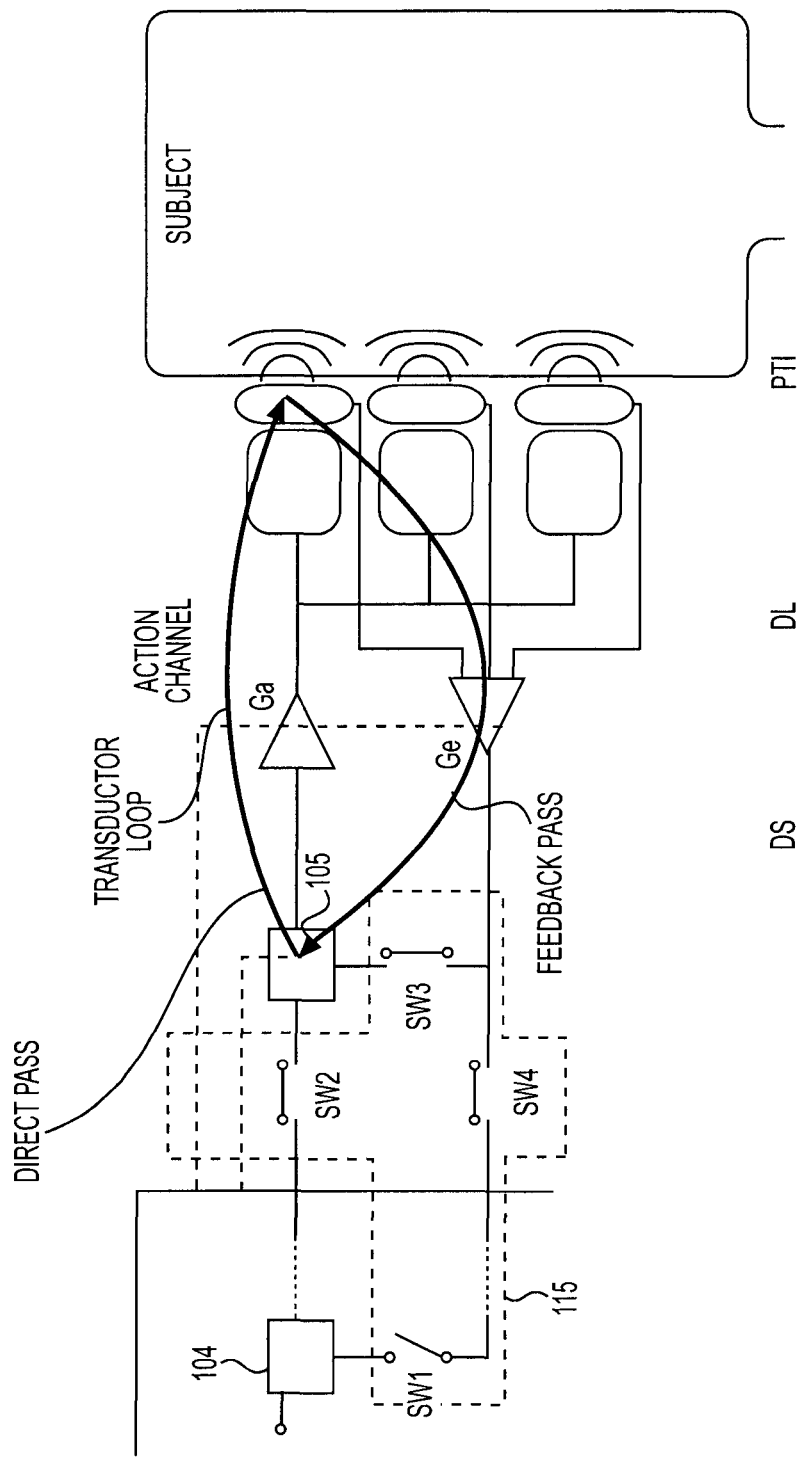
FIG. 9 is a configuration of the system of FIG. 2 showing switch positions for a transducer loop for a distributed stimulus.

FIG. 6 is a configuration of the system of FIG. 2 showing switch positions for a channel loop for a single point stimulus. FIG. 7 is a configuration of the system of FIG. 2 showing switch positions for a transducer loop for a single point stimulus. FIG. 8 is a configuration of the system of FIG. 2 showing switch positions for a channel loop for a distributed stimulus. FIG. 9 is a configuration of the system of FIG. 2 showing switch positions for a transducer loop for a distributed stimulus. Switches SW1, SW2, SW3 and SW4 open or close per commands from control devices 104 and 105 to create the various types of loops within the configurable signal pathway 115. These direct loops are configured in a pure trans-immitance way (PTI), (FIGS. 3, 4, 6-9). A non-limiting example of a direct loop provides an audio signal forming an auditory stimulus and involving an auditory perception.

FIGS. 8 and 9 illustrate three (3) distinct activator/sensor pairs for providing distributed stimuli. In a variant, three (3) separate SPS loops may be used to provide the same type of stimuli.

Figure 10A:
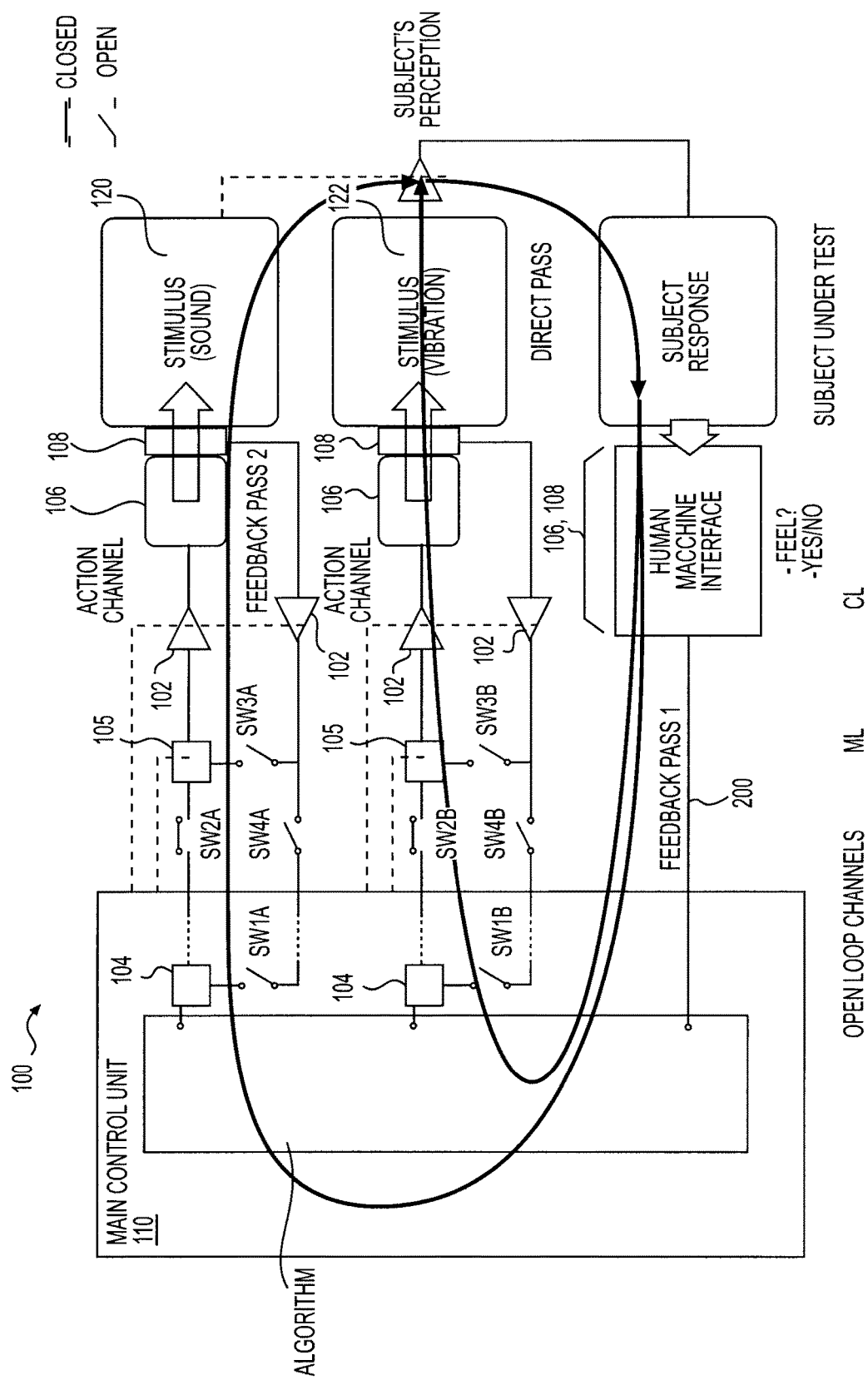
FIGS. 10A, 10B and 10C show various loop configuration examples of the system of FIG. 2.
Figure 10B:
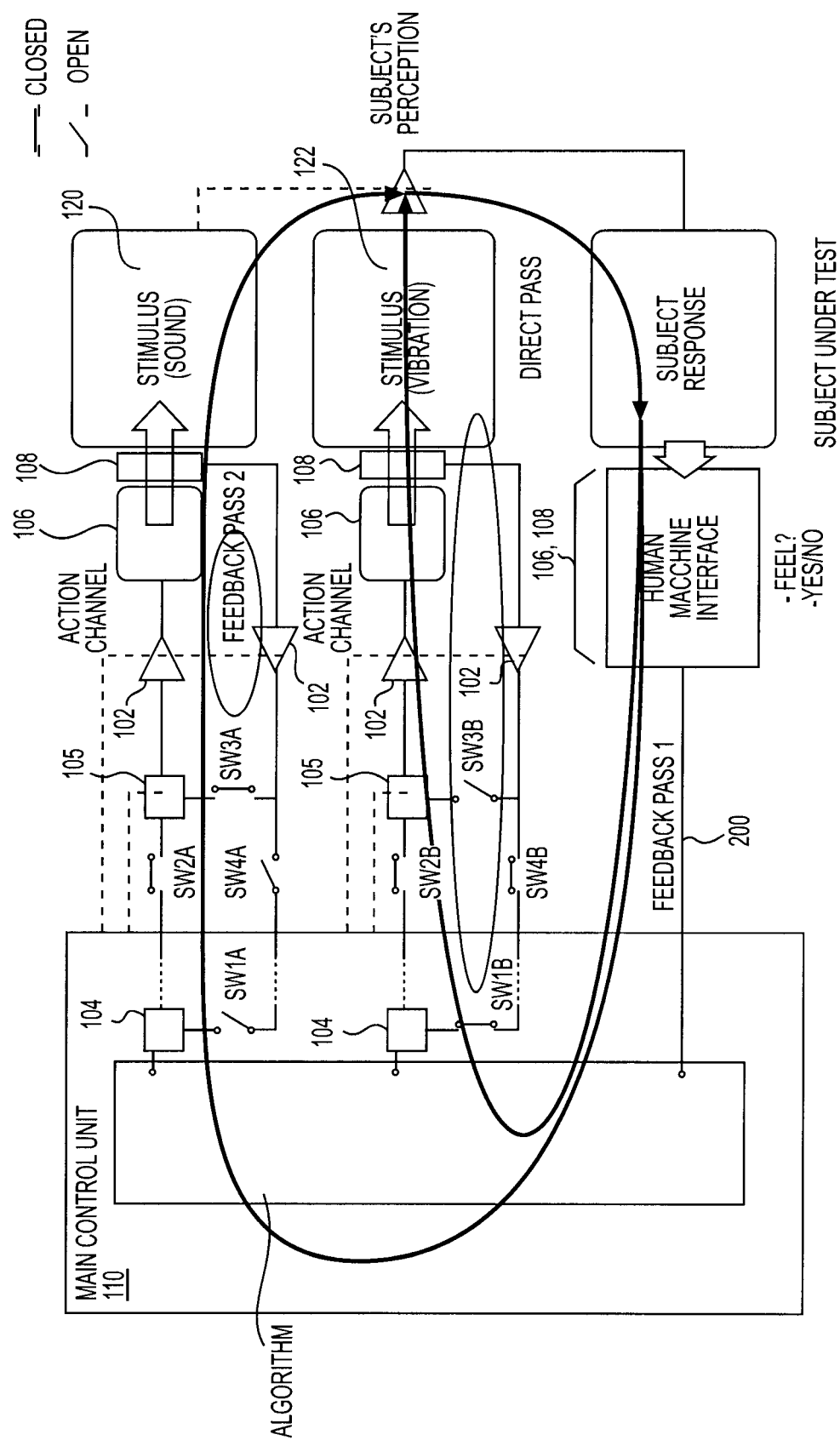
Figure 10C:
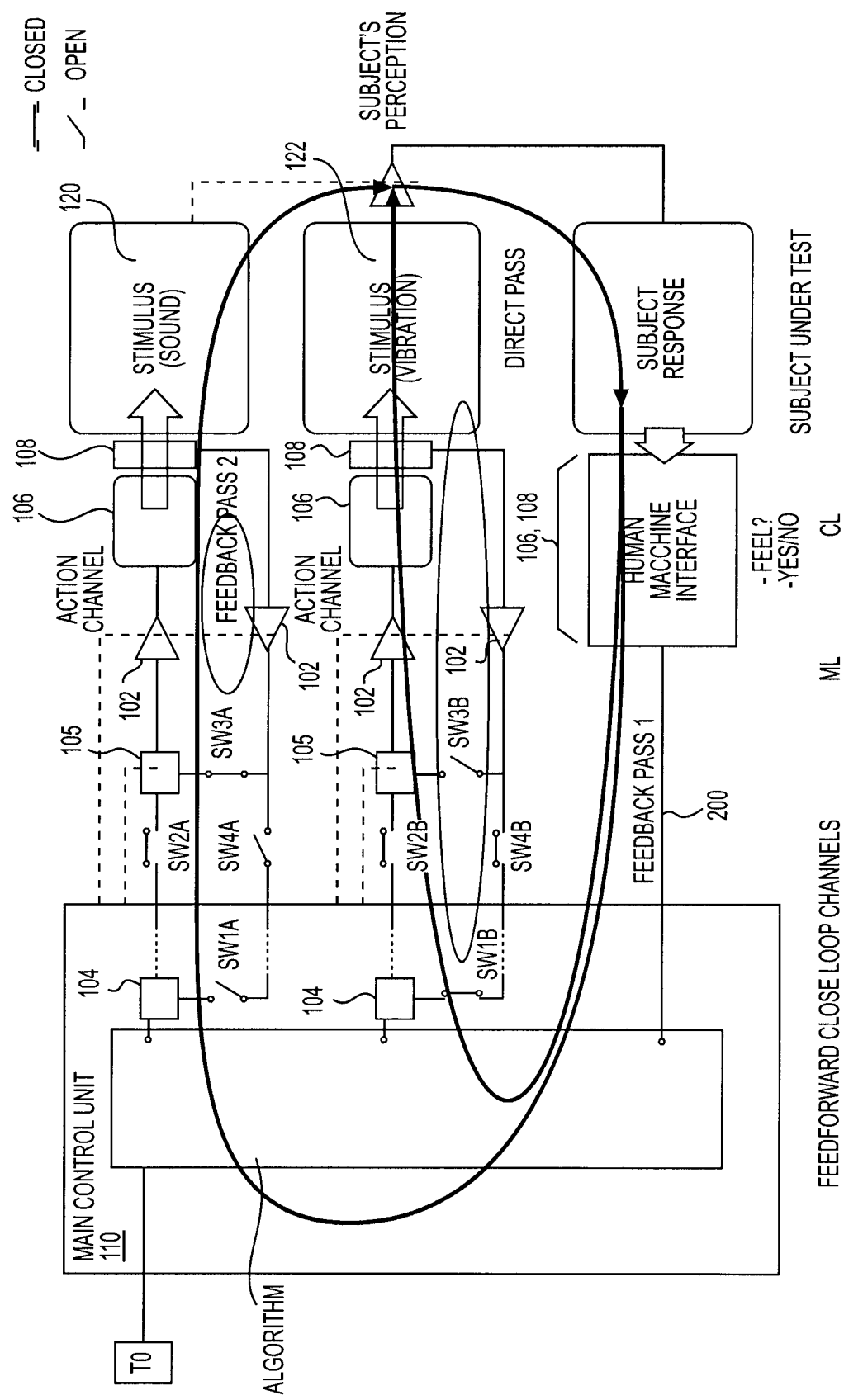

FIGS. 10A, 10B and 10C show various loop configuration examples of the system 100 of FIG. 2. In these Figures, mixed loops (ML) are configured in cross-immitance (CI). They may for instance provide an audio signal causing an auditory stimulus 120 and involving a tactile perception 122 or an audio signal causing a tactile stimulus (from the inherent vibration of the audio signal) and involving a visual perception.

Switches SW1A, SW2A, SW3A and SW4A are part of the configurable signal pathway 115 for a first action channel. Switches SW1B, SW2B, SW3B and SW4B are part of the configurable signal pathway 115 for a first action channel. On FIG. 10A, stimulus channels are in open loop as evidenced by the opening of switches SW4A and SW4B in feedback paths for these channels. A feedback channel 200 is provided to return information about a response of the subject. In contrast, FIGS. 10B and 10C show the closing of switches SW4B and SW1B to create closed loop channels within the stimulus channels, creating feedback paths within the stimulus channel in addition to the feedback channel 200. Both FIGS. 10B and 10C show that feedback paths within the stimulus channels can consist of transducer loops or channel loops. FIG. 10C also show the addition of a variable T0 representing a temperature, provided by a temperature sensor, of the environment surrounding the subject. This addition turns the system 100 into a feed-forward system, in which the main control unit 110 acquires the capability of modifying the system's behavior as function of T0. For instance, the system 100 may have the capability to 'learn" which configuration is most efficient as T0 varies. The system 100 therefore has the capability to evaluate its performance and manage the configuration accordingly.

The system 100 of FIGS. 10A, 10B and 10C can be configured to operate in open loop or close loop modes, providing transducer loops, channel loops or a combination thereof, with or without addition of a parameter for feedforward operation. A large number of distinct configurations may thus be defined.

In a variant, the system 100 may apply stimuli using any interface speaker, monitor, and the like. In another variant, the system 100 uses natural stimuli sources to provide surrounding sounds or images.

The loops may be configured with a broad range of positive or negative feedback gains, ranging from very low feedback positive or negative feedback gains, nearing or reaching an open loop, to a very high positive (afferent) or negative (efferent) feedback gains. Feedback gains may vary according predefined (sequential, random, etc.) or adaptive operation modes.

Though FIGS. 2, 10A, 10B and 10C illustrate an embodiment using feedback compensation (as introduced in FIG. 1, top part), another embodiment of the system 100 may be provided with feedforward compensation (as introduced in FIG. 1, bottom part). FIG. 10C actually shows both feedback and feedforward compensation.

Figure 11:
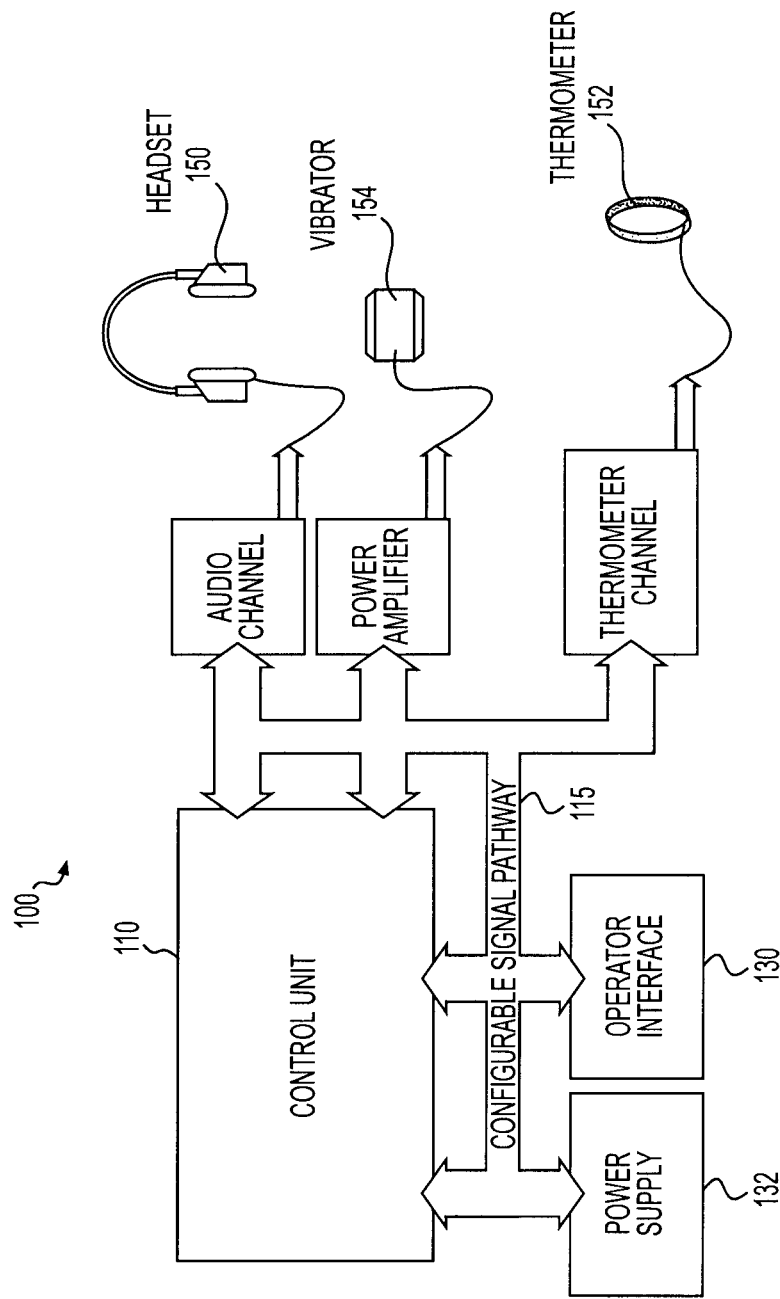
FIG. 11 is a block diagram illustrating an example application of the system of FIG. 2 for stimulating a subject.
Figure 12:
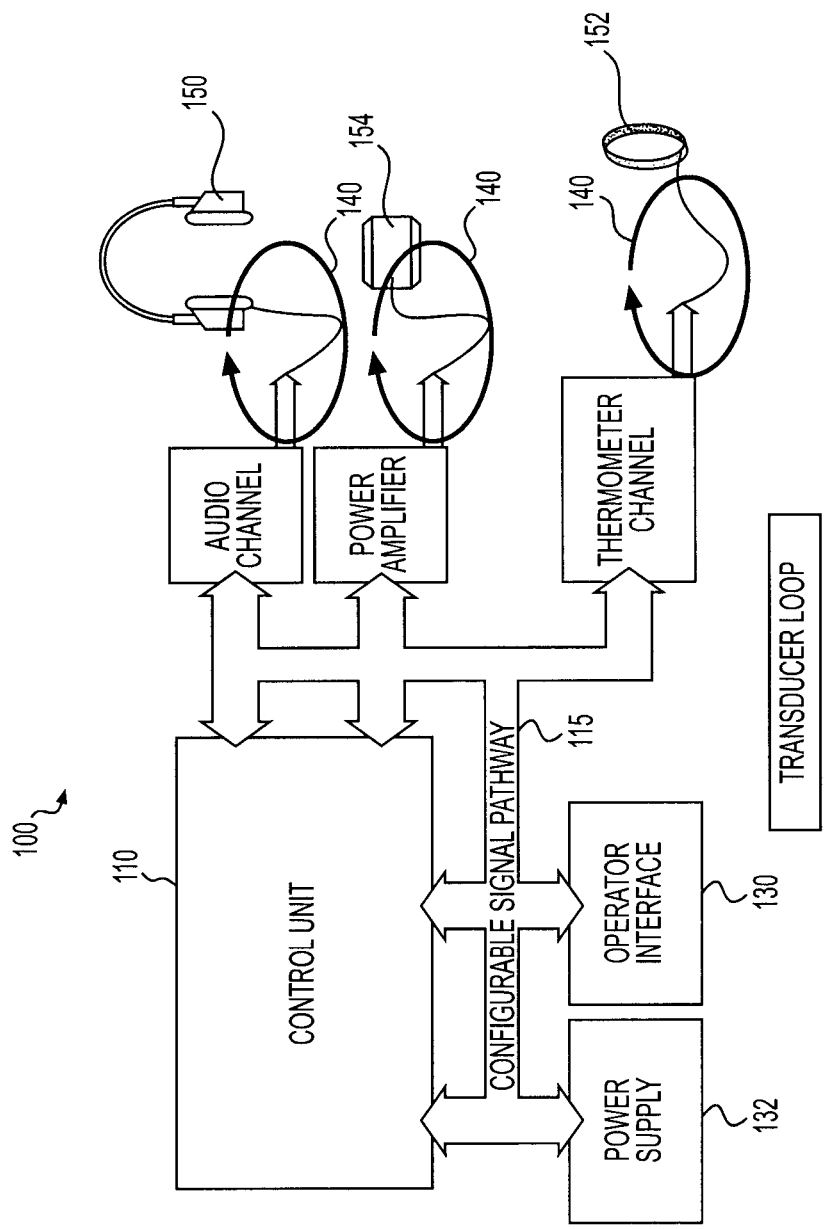
FIG. 12 is an illustration of transducer loops in the application of FIG. 11.
Figure 13:
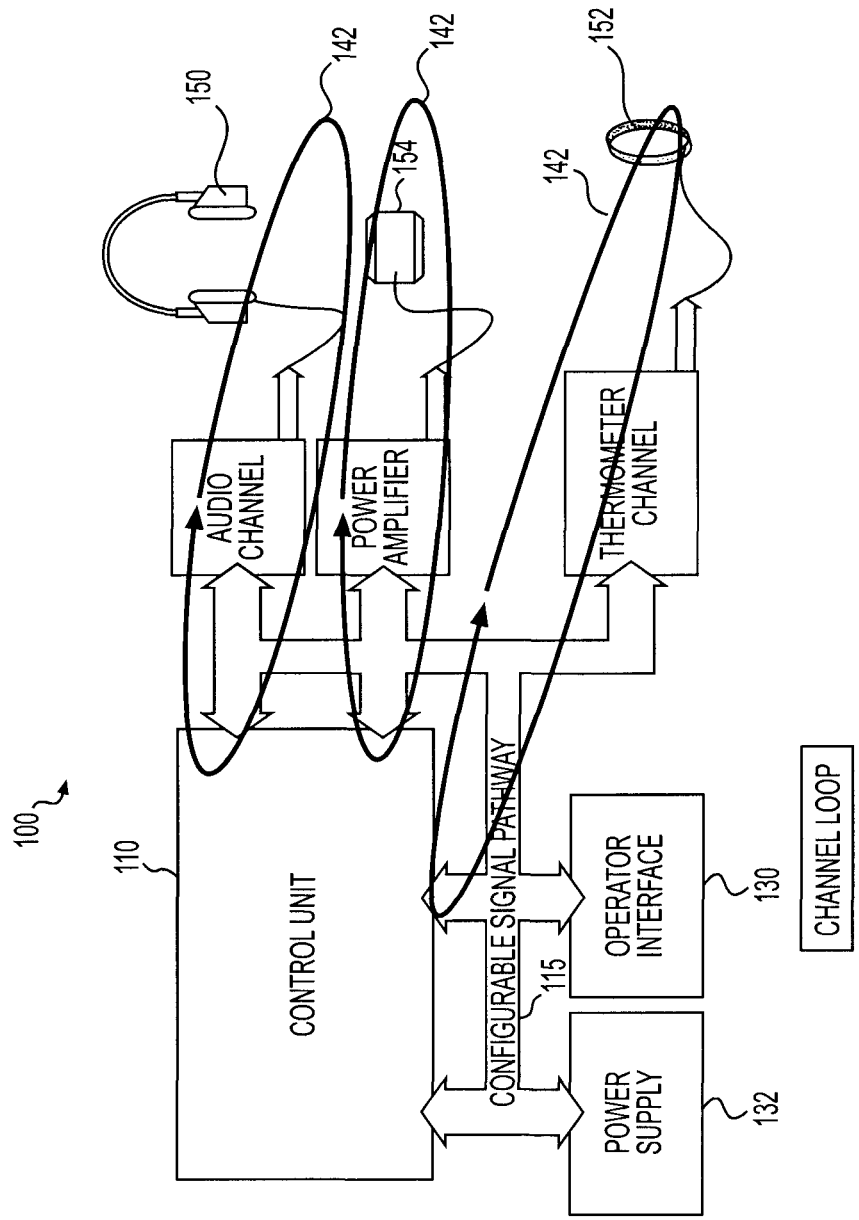
FIG. 13 is an illustration of channel loops in the application of FIG. 11.
Figure 14:
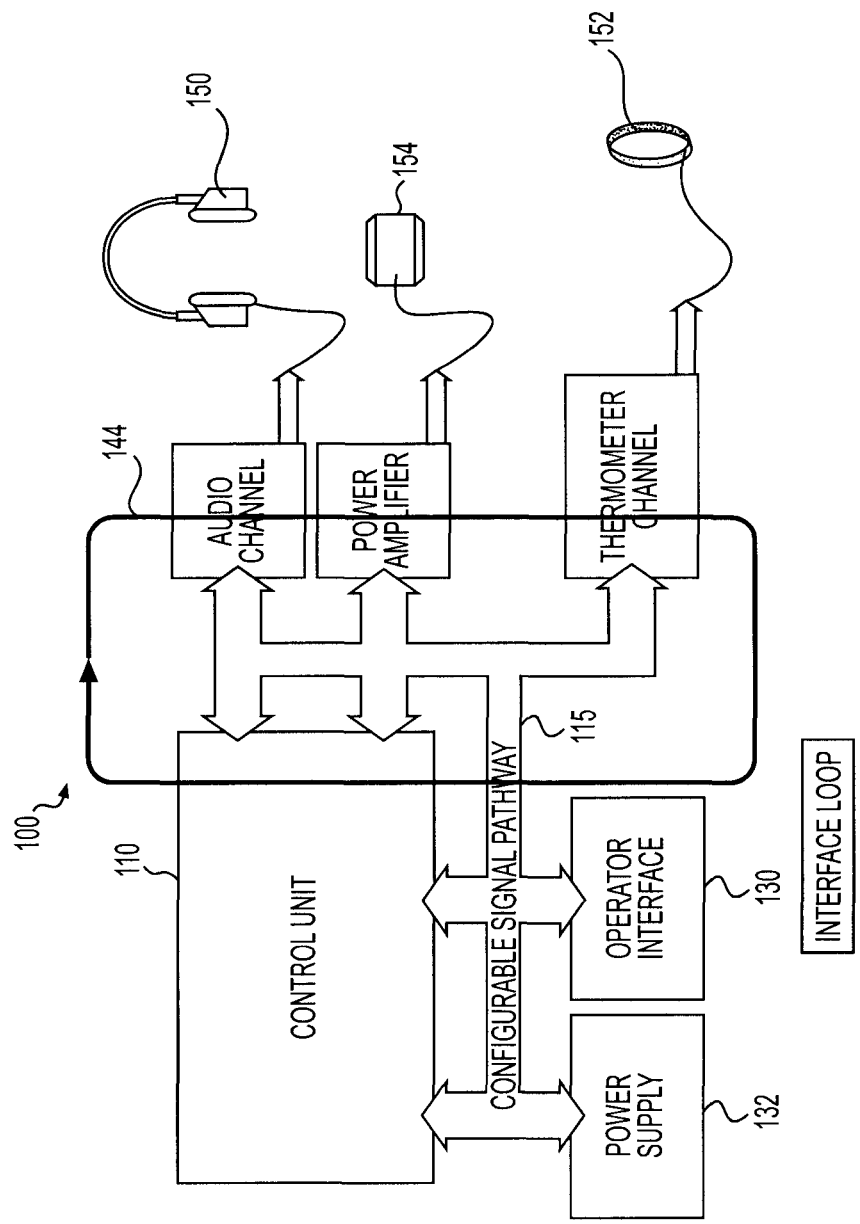
FIG. 14 is an illustration of an interface loop in the application of FIG. 11.
Figure 15:
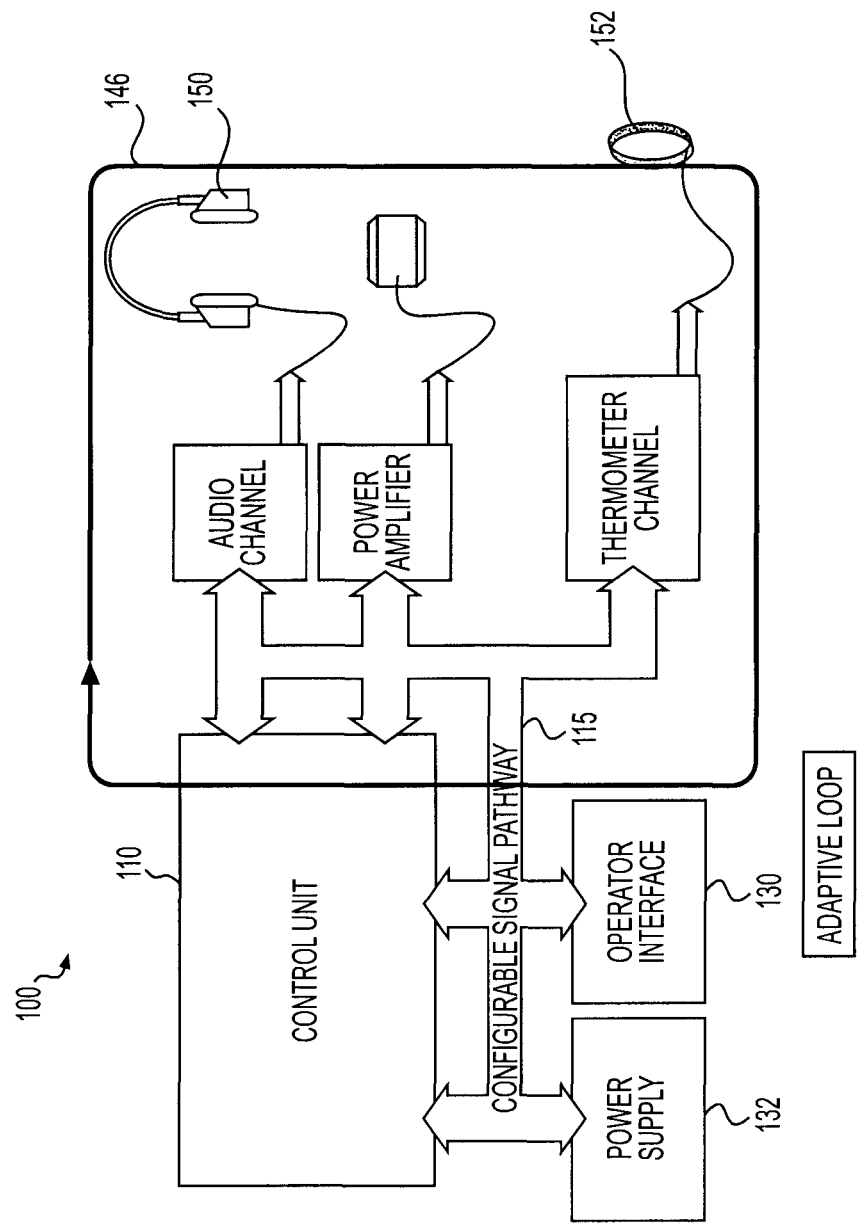
FIG. 15 is an illustration of an adaptive loop in the application of FIG. 11.

A general operation of the system 100 will now be described with reference to FIG. 11 to FIG. 15. FIG. 11 is a block diagram illustrating an example application of the system of FIG. 2 for stimulating a subject. FIG. 12 is an illustration of transducer loops in the application of FIG. 11. FIG. 13 is an illustration of channel loops in the application of FIG. 11. FIG. 14 is an illustration of an interface loop in the application of FIG. 11. FIG. 15 is an illustration of an adaptive loop in the application of FIG. 11. Considering at once FIGS. 11 to 15, a non-limiting example shows a provision of auditory, tactile and visual stimuli to a subject while surface thermometer provides feedback from the subject to the system 100.

For purposes of simplicity and clarity, operation of the system 100 is described in relation to a particular, non-limiting example involving auditory, tactile, and visual stimuli actuators and a surface thermometer configuring the different channels. Stages associated with these channels are equipped with sensors (microphone, accelerometer, heater, and light sensor, electric feedback networks) configured as feedback loops. Extending the operation of the system 100 to several, simultaneous stimulations using various numbers of channel/stimulation modules and stimulations devices is also contemplated.

Experiments are pre-defined and implemented as software tools in the main control unit 110. Loop configurations are defined by the configurable signal pathway 115, which is managed by the main control unit 110.

The main control unit 110 is connected to a power supply 132. It evaluates several involved variables, processes statistics, and manages configuration modes of the system 100. The main control unit 110 also manages an operator interface 130 and the configurable signal pathway 115 that provides connection between the operator interface 130 and other components of the system 100.

The configurable signal pathway 115, which is managed by the operator interface 130 connected to the main control unit 110, links analog and digital signals that configure the loops, define the operation modes of the system 100, controls channel parameters and establishes functional operations involving the system 100 and the subject under test.

Input-output blocks act as an interface between the input-output blocks and the channel actuators or channel sensors.

Input-output transducers act as channel actuators or sensors and include, for example headsets, vibrators, thermometers, monitors, and the like. The input-output transducers are usable in a closed loop operation.

The operator interface 130 is a human-machine interface, including for example a monitor, a keypad, a pointing device, and the like, all of which are not shown but well-known. Its monitor may also be used as visual stimuli activator.

Configured loops are defined in function of experiments to be performed on a subject and may be switched from one configuration to another in function of the evolution of a variable or in an adaptive way, depending for example on a voluntary or involuntary response of the subject response.

Transduction loops 140 as shown on FIG. 12 are used to stabilize response from the activator response, both in cases of single point direct loop for auditory stimuli and of distributed direct loop for tactile stimuli. In more details, a transducer loop 140 stabilizes the activator action itself. It may for instance improve its frequency response, linearize its phase shift to avoid harmonic distortion, or flatten its gain along the spectrum, reducing its parameters drifts when environment temperature changes, and the like. These improvements are referred to a signal reaching a corresponding input relay (the closer control device 105) as reference, that is, the signal present at the reference input of the transduction loop. If that signal contains any distortion, the transducer reproduces the distortion. The transducer itself does not introduce further significant distortion.

Channel loops 142 as shown on FIG. 13 are used to stabilize variable responses in the case of direct loops. Adding a channel loop 142 improves the overall channel performance. Now, even the signal present at the reference input of the transduction loop mentioned herein above presents further reduced distortion in comparison to when the only transduction loop is used because of the addition of negative feedback action. The transduction loops 140 have fast reaction times while the channel loops 142 provide a higher level of control. Longer loops present longer propagation times.

An interface loop 144 as shown on FIG. 14 stabilizes a combination of variable responses in the case of mixed loops.

An adaptive loop 146 as shown on FIG. 15 has parameters, such as again, a phase shift, and the like, that depends at least in part on responses or reactions from the subject.

In operation of the system 100, an operator activates the main control unit 110, for example through depression of a push-button or key located at the operator interface 130. Using the operator interface 130, the operator may select a desired type of loop to activate a stimulation of the subject such as, for example, a visual stimulation, an acoustic stimulation, a vibratory stimulation, and the like. For instance, an auditory stimulus may be activated via a single point direct loop (as shown on FIG. 3) and a tactile stimulus may be activated via a distributed direct loop (as shown on FIG. 4). Then, the operator may connect a stimulation device, corresponding to the selected type of stimulation, to the main control unit 110 via the appropriate loops. The example of FIGS. 12-15 includes three (3) transducer loops 140, three (3) channel loops 142, and one (1) interface loop 144 forming an adaptive loop 146. The main control unit 110 automatically configures the system modes, evaluates the involved variables, calculates statistics, and establishes links between components of the system 100 through the configurable signal pathway 115.

The system 100 of FIG. 2 is very flexible with regards to the number of stimulations. It is also easy to operate and may be easily transported by a person.

More specifically, the example of the system 100 as illustrated in FIG. 11 simultaneously generates different stimulations. A subject can wear the main control unit 110 on a belt fixed around his waist. A first stimulation device in the form of an acoustic stimulation device 150, a sensor device in the form of a temperature measurement device 152 and a second stimulation device in the form of a vibrator 154 are connected to the main control unit 110 through the configurable signal pathway 115.

FIGS. 12-15 show the implementation of several loops to have are implemented a subject under the influence of two simultaneous sensory simulations using the system 100 of FIG. 2. In FIGS. 12-15, the subject is under the influence of two stimulations simultaneously applied by the acoustic stimulation device 150, the vibratory stimulation device 154 and the temperature is sensed by the thermometer 152. The set-up of FIGS. 12-15 has been used in a laboratory to demonstrate that tactile sensitivity of the subject may be improved via acoustic stimulation.

Of course, it should be understood that many other such combinations of stimulations are possible, with two (2) or even more simultaneously applied stimuli.

The concept of the Fulcrum Principle may be used for improving a subject's sensory, reflex and/or motor mechanisms, more specifically the general sensitivity and postural balance of the subject. The present disclosure shows an improvement of the sensitivity of a subject's sensory, reflex and/or motor mechanism by using a facilitation signal to stimulate another different sensory mechanism. A stimulus loops interface is used to control the level of the facilitation signal.

For the Fulcrum Principle to occur in a nonlinear system, the nonlinear system needs three (3) parameters: (i) a threshold, (ii) a facilitating signal, which may either be randomly determined or be deterministic, and (iii) sub-threshold information (i.e an excitatory signal), wherein the sub-threshold information relates to an excitatory signal applied to a sensory mechanism and having too low a magnitude (below a threshold) to allow the sensory mechanism to react to that excitatory signal. An optimal amount of an added facilitation signal may yield an optimal enhancement of the excitatory signal detection. Indeed, when too small a facilitation signal is added, the sub-threshold excitatory signal information is still below the threshold and cannot be detected. When too strong a facilitation signal is added to the excitatory signal, the facilitation signal becomes too strong with respect to the information content of the excitatory signal and, therefore, this too strong a facilitation signal will randomize the reactions of the subject's sensory, reflex and/or motor mechanisms in response to the excitatory signal.

A non-limitative aspect of the present disclosure is concerned with stimulating a particular type of sensory mechanism of a subject to improve another type of sensory, reflex and/or motor mechanism of the same subject. Some experiments have shown that applying, as a facilitation signal, an auditory noise to the ear(s) of a subject modulates the tactile sensation of his/her index finger, modulates the electromyographic (EMG) activity of his/her leg muscles and/or modulates the stabilogram sweep area during posture maintenance. In other experiments, the facilitation signal was deterministic and, a harmonic sound to the ears of a subject modulated the tactile sensation of his/her calves. In yet other experiments, a harmonic visual signal to the eyes of a subject modulated the tactile sensation of his/her calves. Therefore, these experiments show that interactions inside the human cortex are Fulcrum Principle-based interactions, which form a multi-sensory integrated system. Under the influence of a facilitation signal in the multi-sensory integrated system, the generalized state of a subject may be enhanced, including the postural balance.

An application of the Fulcrum Principle, when a subject is under the influence of several stimulations, comprises using a facilitation signal for improving the subject's sensitivity to an excitatory signal. The excitatory signal is applied to stimulate a first sensory, reflex and/or motor mechanism of the subject. The facilitation signal is applied to stimulate a second sensory, reflex and/or motor mechanism of the subject 36. A physiological response of the subject 36 is measured at the first sensory, reflex and/or motor mechanism. A level of the facilitation signal is adjusted based on the measured physiological response. For example, for improving the tactile sensitivity of a subject to an excitatory signal, as illustrated in FIG. 11, the subject is provided with an acoustic signal forming a facilitation signal. Adjustment of the acoustic facilitation signal allows for finding the optimal level of improvement of the tactile sensitivity. A procedure using objective physiological responses for finding this optimal level is described in more detail herein below. The skilled reader having the benefit of the present disclosure will appreciate that the expression "optimal level" as applied herein to improvement of the tactile sensitivity or to adjustment of the facilitation signal is intended to represent a desirable or satisfactory level and is not meant to refer to an absolute performance level.

Figure 16:
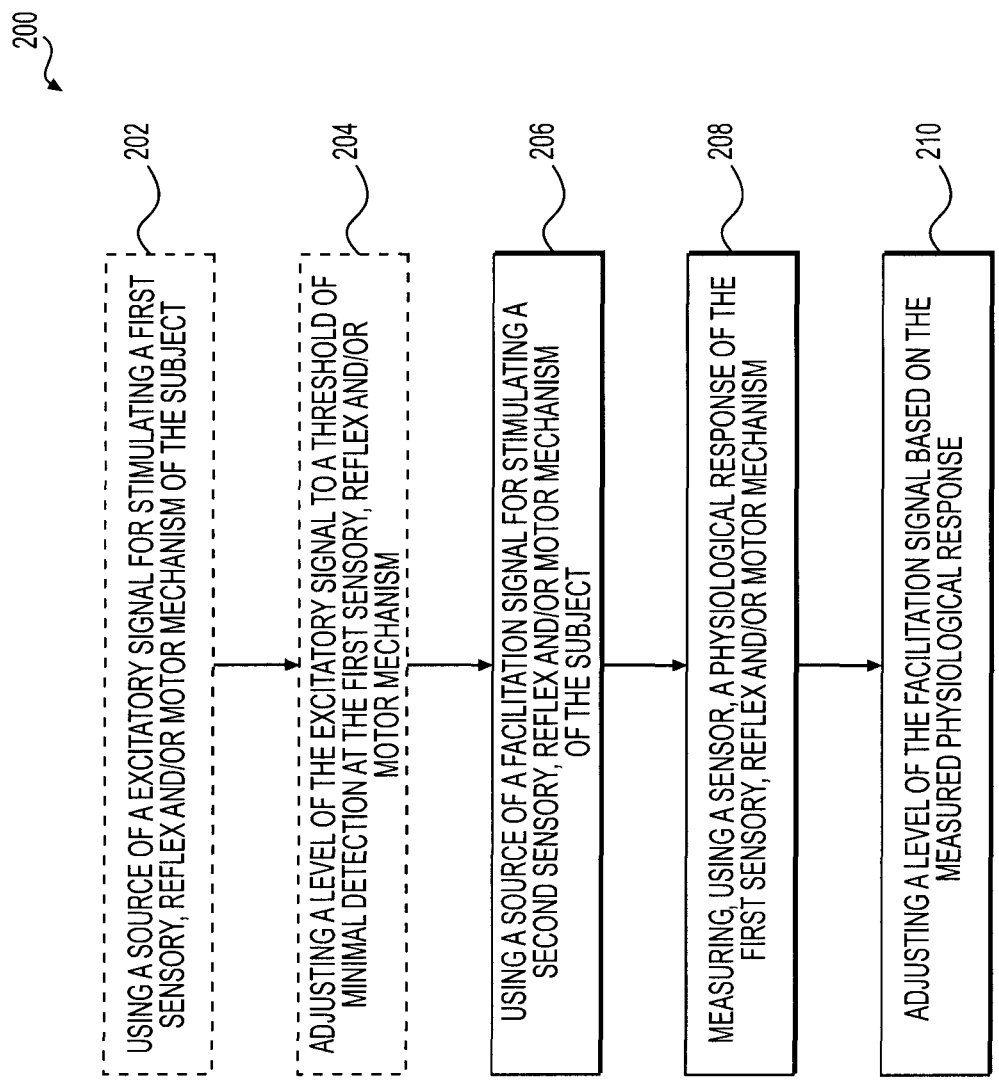
FIG. 16 is a flow diagram of a method for improving sensitivity of a first sensory, reflex and/or motor mechanism of a subject according to an embodiment.

FIG. 16 is a flow diagram of a method for improving sensitivity of a first sensory, reflex and/or motor mechanism of a subject according to an embodiment. A sequence 200 may comprise an operation 202 of using a source of an excitatory signal for stimulating the first sensory, reflex and/or motor mechanism and an operation 204 of adjusting a level of the excitatory signal to a threshold of minimal detection at the first sensory, reflex and/or motor mechanism. Then at operation 206, a source of a facilitation signal is used for stimulating a second sensory, reflex and/or motor mechanism of the subject. Operation 208 comprises using a sensor to measure a physiological response of the first sensory, reflex and/or motor mechanism. Then at operation 210, a level of the facilitation signal is adjusted based on the measured physiological response. The application of the facilitation signal plus the measure of the physiological response provide an adaptive loop, whereby adjusting the level of the facilitation signal improves the sensitivity of the first sensory, reflex and/or motor mechanism due to the Fulcrum Principle interactions. This is an example of a mixed loop.

In the sequence 200, the facilitation signal may for example be randomly determined or be deterministic signals and the physiological response may for example comprise a temperature measured at the first sensory, reflex and/or motor mechanism.

In a variant of the sequence 200, the operation 204 of adjusting the level of the excitatory signal to a sub-threshold level at the first sensory, reflex and/or motor mechanism may comprise reducing the level of the excitatory signal until it is no longer detectable by the subject. Once at sub-threshold level the machine interface increases automatically or the subject increases manually the facilitation signal. As the facilitation signal amplitude increases, the excitatory signal sensation increases accordingly, up to a point where the sensation is at a maximum. This point is called a point of maximum sensation. If the facilitation signal increases even more, the excitatory signal sensation begins to decrease until it faints away again. This point is the noise threshold level and it will be the new reference. The facilitation signal needs to be applied at least one minute prior switching to the next noise level. The point of maximum sensation would be five decibels below this point. The interface can attenuate the 5 dB automatically by including an electronic attenuator.

Stimulating either of the first or second sensory, reflex and/or motor mechanisms may be made by applying an auditory signal to at least one ear of the subject, by applying a visual signal to at least one eye of the subject, by applying a tactile signal to at least one part of the subject's body, by applying an electromagnetic signal to at least one area of the subject's body, by applying a thermal signal to at least one area of the subject's body, by applying a vibratory signal to at least one area of the subject's body, by providing for the subject to detect an odor, or by providing for the subject to taste a gustatory sample.

Stimulation of either of the first or second sensory, reflex and/or motor mechanisms may be made directly applying the excitatory signal or the facilitation signal to a particular area of the subject's body.

Stimulation of the first sensory, reflex and/or motor mechanism may also be made by differentially applying the excitatory signal by stimulating two different areas of the subject's body in order to stimulate a region of the subject's body between the two different areas. Stimulation of the first sensory, reflex and/or motor mechanism may further be made by distributing the excitatory signal by stimulating several areas of the subject's body in order to stimulate a region of the subject's body covered by the several areas. Stimulation of the first sensory, reflex and/or motor mechanism may alternatively be made by distributing a plurality of different excitatory signals on the subject's body.

Stimulation of the second sensory, reflex and/or motor mechanism may also be made by differentially applying the facilitation signal by stimulating two different areas of the subject's body in order to stimulate a region of the subject's body between the two different areas. Stimulation of the second sensory, reflex and/or motor mechanism may further be made by distributing the facilitation signal by stimulating several areas of the subject's body in order to stimulate a region of the subject's body covered by the several areas. Stimulation of the second sensory, reflex and/or motor mechanism may alternatively be made by distributing a plurality of different facilitation signals on the subject's body.

Figure 17:
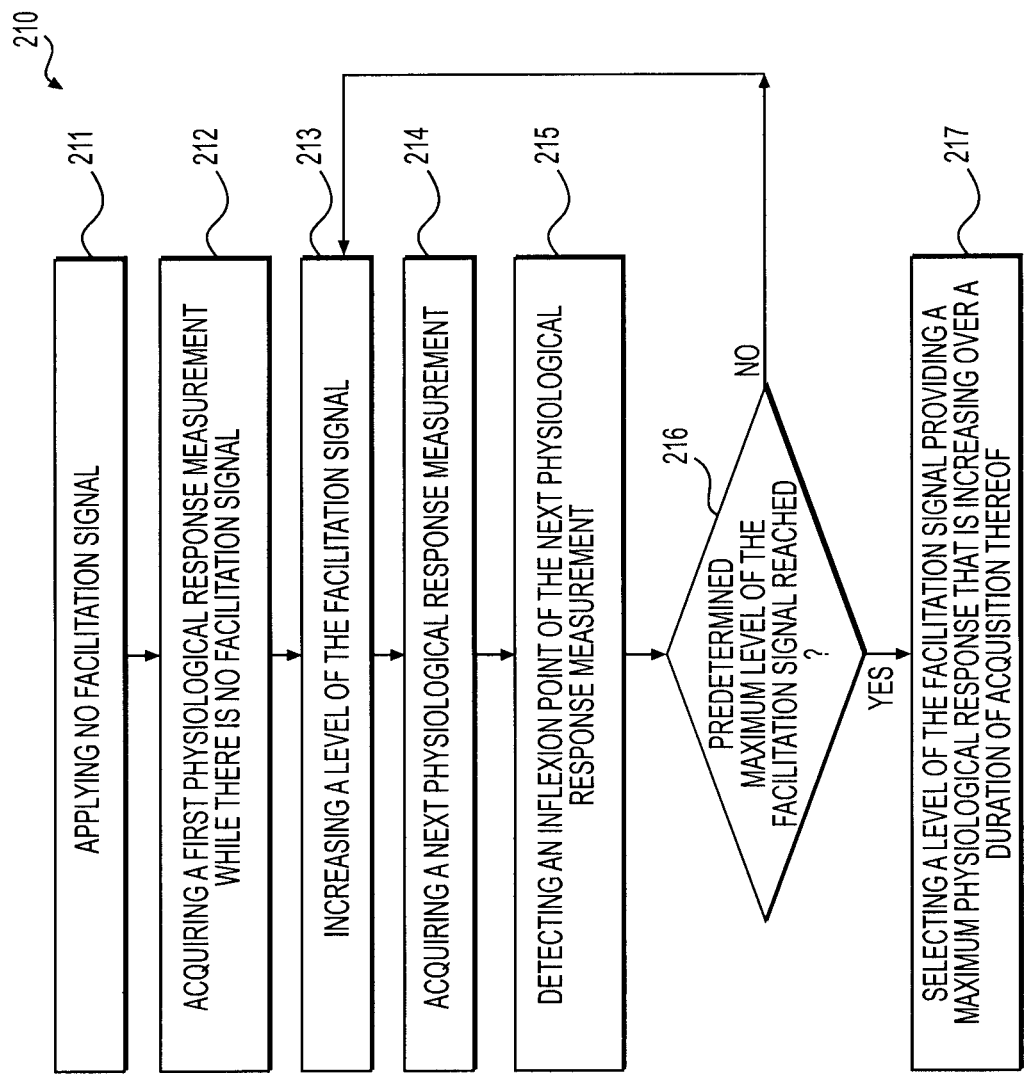
FIG. 17 is flow diagram of a detailed sequence for adjusting a level of the facilitating signal based on the measured physiological response according to another embodiment.

FIG. 17 is flow diagram of a detailed sequence for adjusting a level of the facilitation signal based on the measured physiological response according to another embodiment. In an embodiment, operation 210 of FIG. 16 may comprise operations 211-17. Operation 211 comprises applying no facilitation signal at first. Operation 212 comprises acquiring a first physiological response measurement while there is no facilitation signal. Then operation 213 involves increasing a level of the facilitation signal, after which operation 214 comprises acquiring a next physiological response measurement. An inflexion point of the next physiological response measurement is detected at operation 215. Following detection of an inflexion point for the present level of the facilitation signal, if a predetermined maximum level of the facilitation signal is not reached at operation 216, operations 213, 214 and 215 are repeated. After the predetermined maximum level of the facilitation signal has been reached at operation 216, operation 217 comprises selecting a level of the facilitation signal providing a maximum physiological response that is increasing over a duration of acquisition thereof to complete adjusting the level of the facilitation signal based on the measured physiological response.

In a variant, operation 214 of acquiring each physiological measurement may be performed in real time. The skilled reader having the benefit of the present disclosure will be able to adjust the acquisition time within this range or in a broader range, according to the particular circumstances of an implementation of the method. In the same or other variants, selection at operation 217 of a level of the facilitation signal providing a maximum physiological response that is increasing over a duration of acquisition thereof may comprise calculating an integral of each physiological response measurement over its duration of acquisition, calculating a gradient of each physiological response, wherein the gradient is normalized by its own magnitude, calculating for each physiological response a product of the integral with its gradient and then selecting a highest positive product.

Of course, the system 100 and its components, introduced in the foregoing description of FIGS. 2-4, 6-15, and variants of such system 100 and components, may be used to apply the method and improve sensitivity of a first sensory, reflex and/or motor mechanism of a subject. The system 100 may thus comprise a source and the like of a facilitation signal for stimulating a second sensory, reflex and/or motor mechanism of the subject, a sensor for measuring a physiological response of the first sensory, reflex and/or motor mechanism and a controller, for example the main control unit 110 or a controller built within the main control unit 110, for adjusting a level of the facilitation signal based on the measured physiological response. As an example, a sensor may be configured to measure a temperature at the first sensory, reflex and/or motor mechanism.

The system 100 may adjust the level of the facilitation signal improves the sensitivity of the first sensory, reflex and/or motor mechanism of a subject due to the Fulcrum Principle interactions. In this system 100, the source of the facilitation signal may comprise a visual stimulation device, a vibratory stimulation device, an electromagnetic stimulation device, a thermal stimulation device, a tactile stimulation device, an acoustic stimulation device, an odor (e.g. a perfume) placed within a short distance of the subject, or a gustatory sample that the subject may taste. The source of the facilitation signal may be configured to a direct stimulation to a particular area of the subject's body. Alternatively, the system 100 may comprise two sources for applying a differential facilitation signal by stimulating two different areas of the subject's body in order to stimulate a region of the subject's body between the two different areas. In another alternative, the system 100 may comprise a plurality of sources for applying a distributed facilitation signal by stimulating several areas of the subject's body in order to stimulate a region of the subject's body covered by the several areas or a plurality of sources of different types for applying a plurality of different facilitation signals to the patient's body.

The controller of the system 100 may be capable of performing or controlling the performance of all operations of the sequence of FIGS. 16 and 17, including without limitation performing each physiological measurement acquisition over a duration in a range between one (1) and two (2) minutes, and also including without limitation selecting a level of the facilitation signal providing a maximum physiological response that is increasing over a duration of acquisition thereof by a calculation of an integral of each physiological response measurement over its duration of acquisition, a calculation of a gradient of each physiological response, wherein the gradient is normalized by its own magnitude, a calculation of for each physiological response a product of the integral with its gradient and a selection of a highest positive product.

The system 100 may comprise a source and the like, of an excitatory signal for stimulating the first sensory, reflex and/or motor mechanism, in which case the controller is configured to, before adjusting the level of the facilitation signal, adjust a level of the excitatory signal to a sub-threshold level at the first sensory, reflex and/or motor mechanism. The controller may also be configured to adjust the level of the excitatory signal to the sub-threshold at the first sensory, reflex and/or motor mechanism by reducing the level of the excitatory signal until it is no longer detectable by the subject. Once at sub-threshold level the machine interface increases automatically or the subject increases manually the facilitation signal. As the facilitation signal amplitude increases the excitatory signal sensation increases accordingly, up to a point where the sensation is maximum, this is the point of maximum sensation. If the facilitation signal increases even more the excitatory signal sensation begins to decrease until the excitatory signal sensation faints away again. This point is the noise threshold level and it will be the new reference. The facilitation signal needs to be applied at least one minute prior switching to the next noise level. The point of maximum sensation would be five decibels below this point. The interface can attenuate the 5 dB automatically by including an electronic attenuator. The source of the excitatory signal may comprise a visual stimulation device, a vibratory stimulation device, an electromagnetic stimulation device, a thermal stimulation device, a tactile stimulation device, an acoustic stimulation device, a source of an odor (e.g. a perfume) placed within a short distance of the subject, or a device providing a gustatory sample that the subject may taste. A stimulator connected to the source of the excitatory signal may apply the excitatory signal to the first sensory, reflex and/or motor mechanism while another stimulator connected to the source of the facilitation signal may apply the facilitation signal to the second sensory, reflex and/or motor mechanism.

The system 100 may also comprise an interface for connecting the system 100 to a computer for transferring thereto information about a stimulation process.

Figure 18:
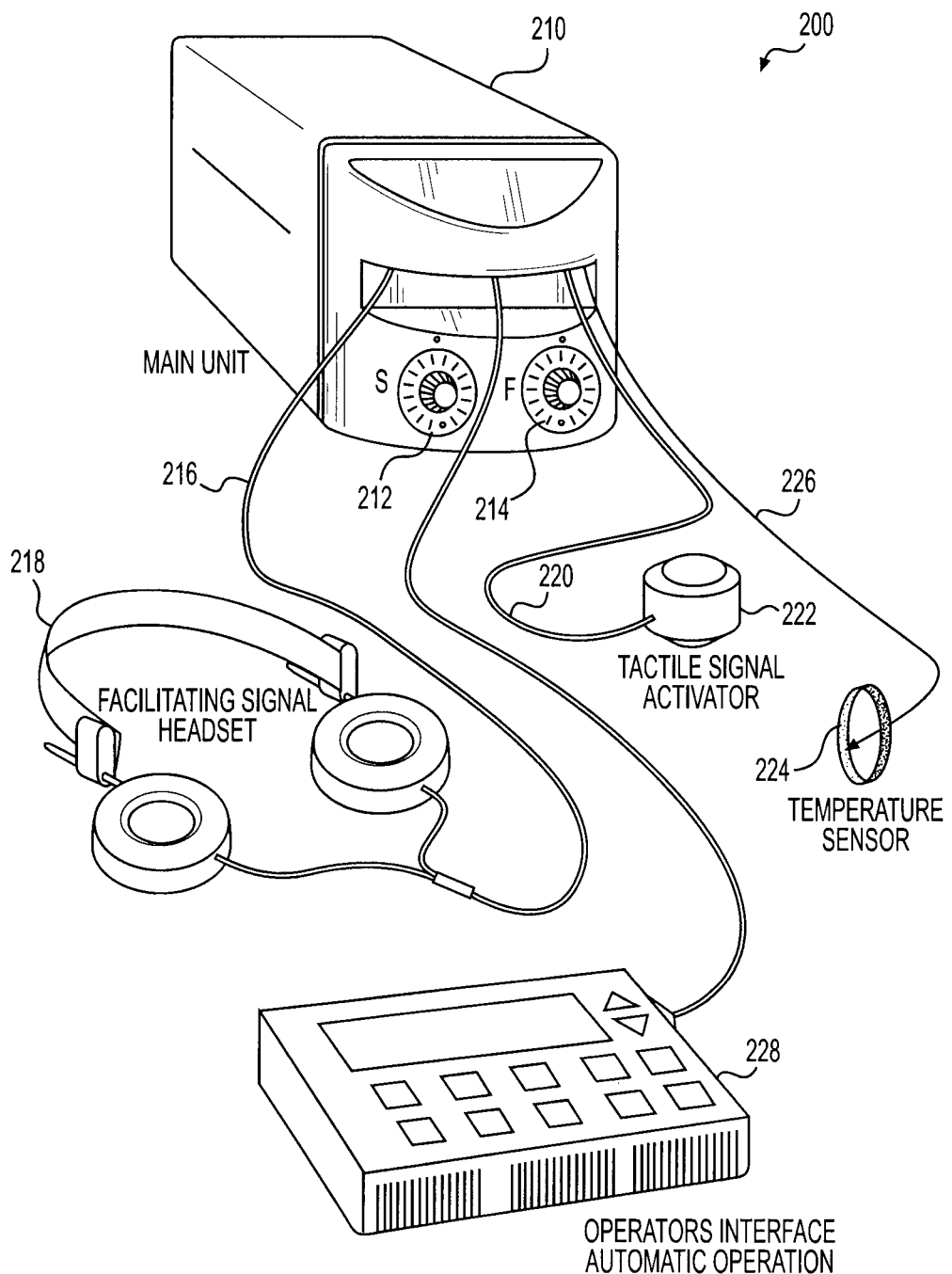
FIG. 18 is a perspective view of a realization of a neurotuner according to an embodiment.
Figure 19:
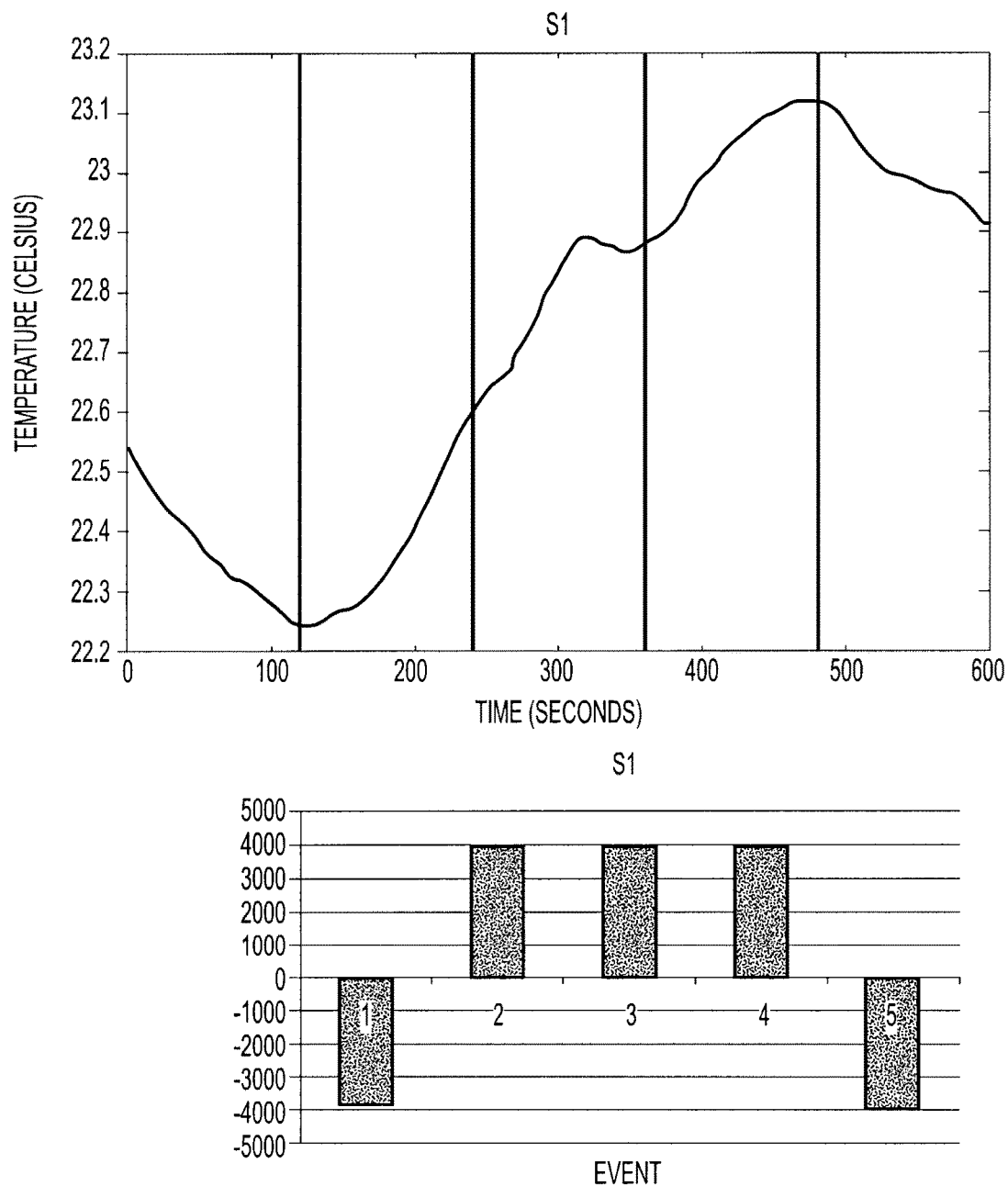
FIGS. 19-24 provide experimental results obtained using the neurotuner of FIG. 18.
Figure 20:
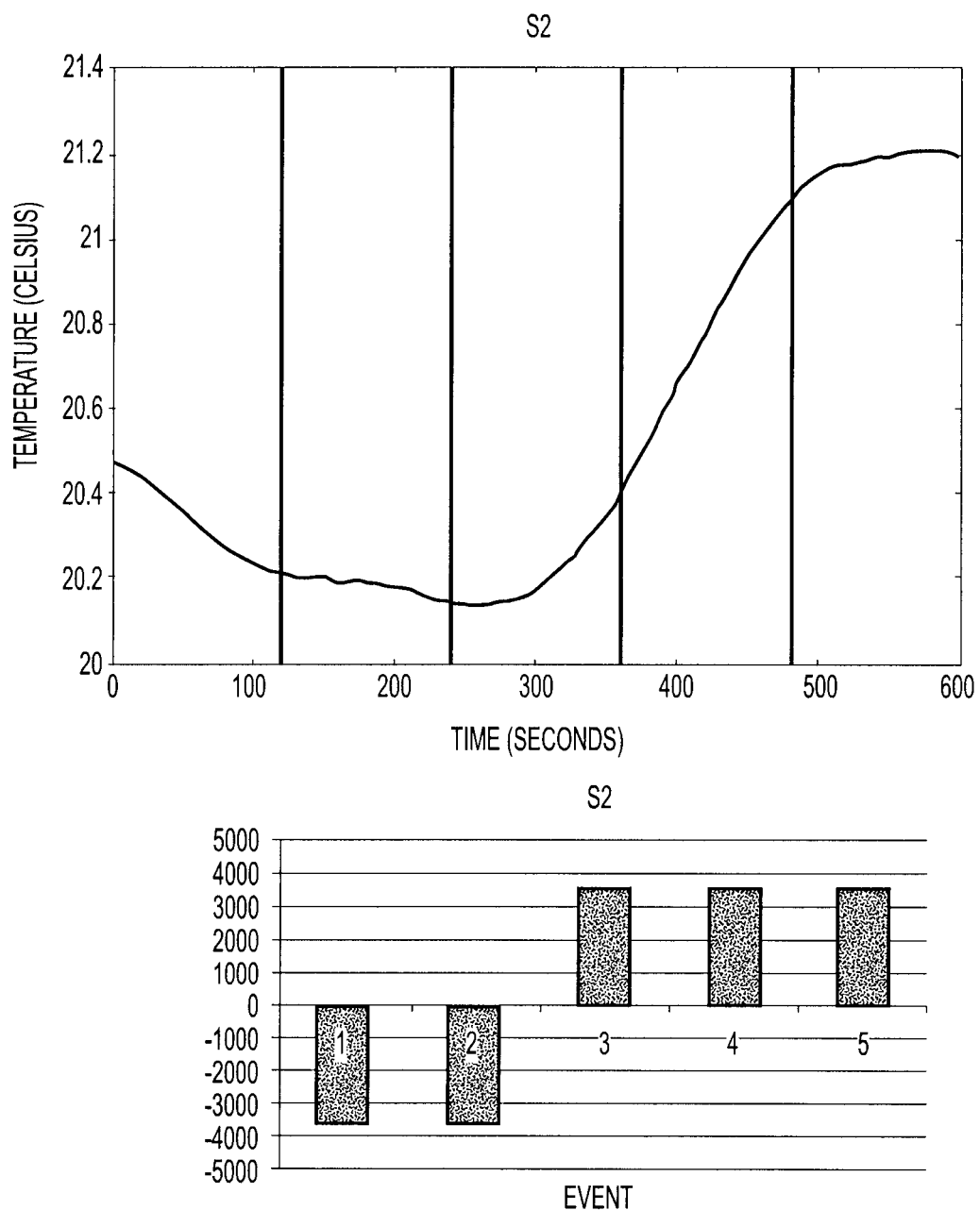
Figure 21:
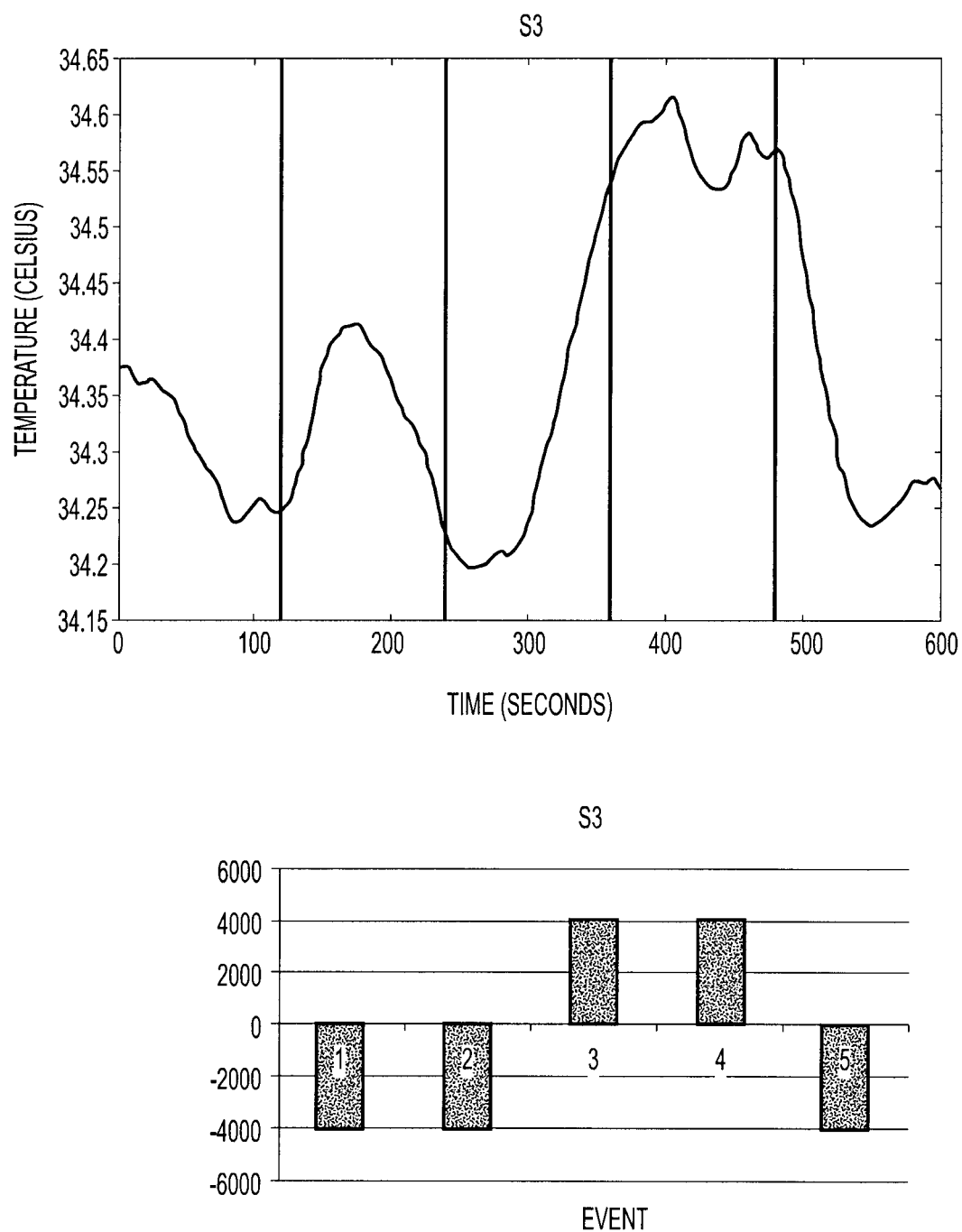
Figure 22:
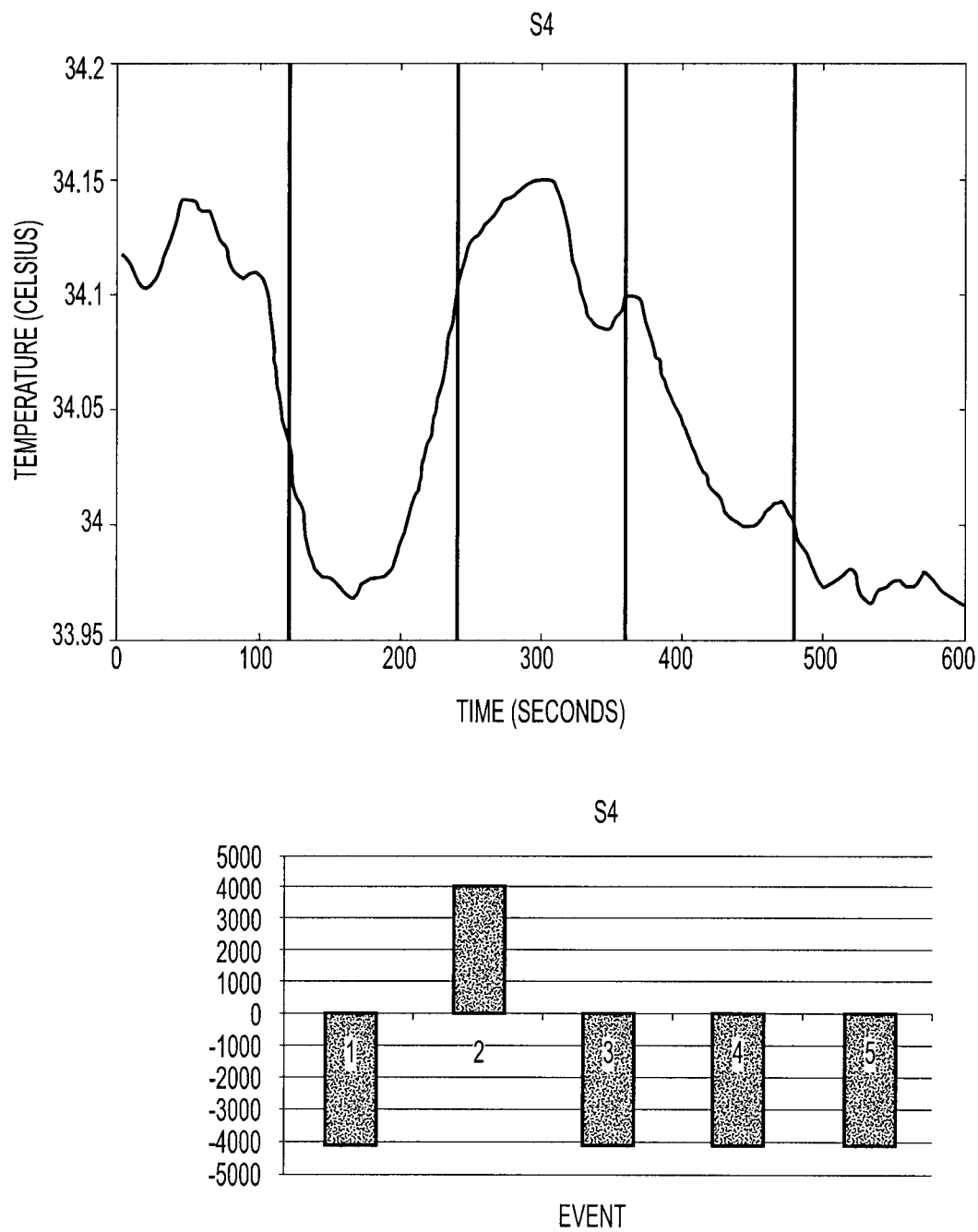
Figure 23:
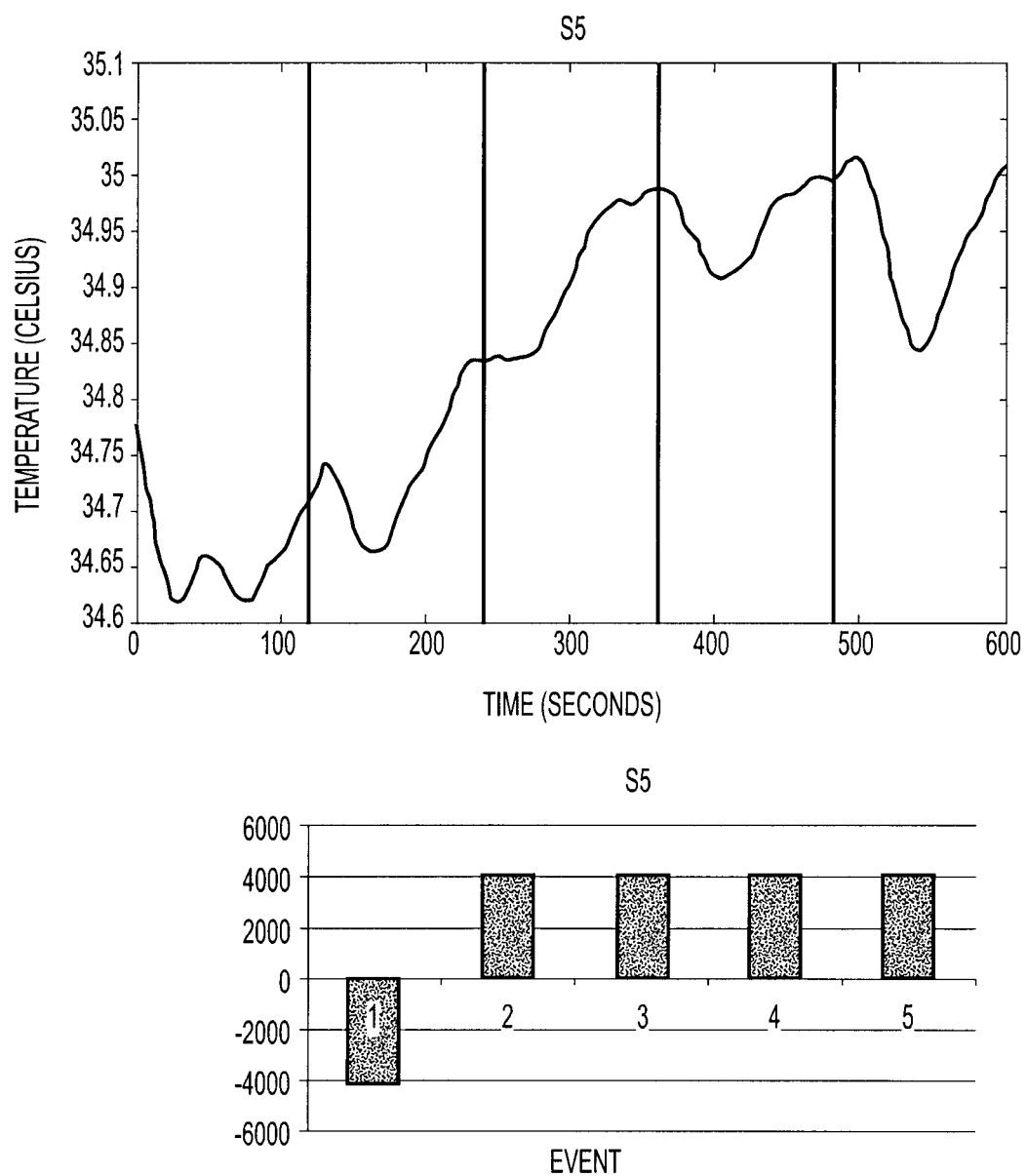
Figure 24:
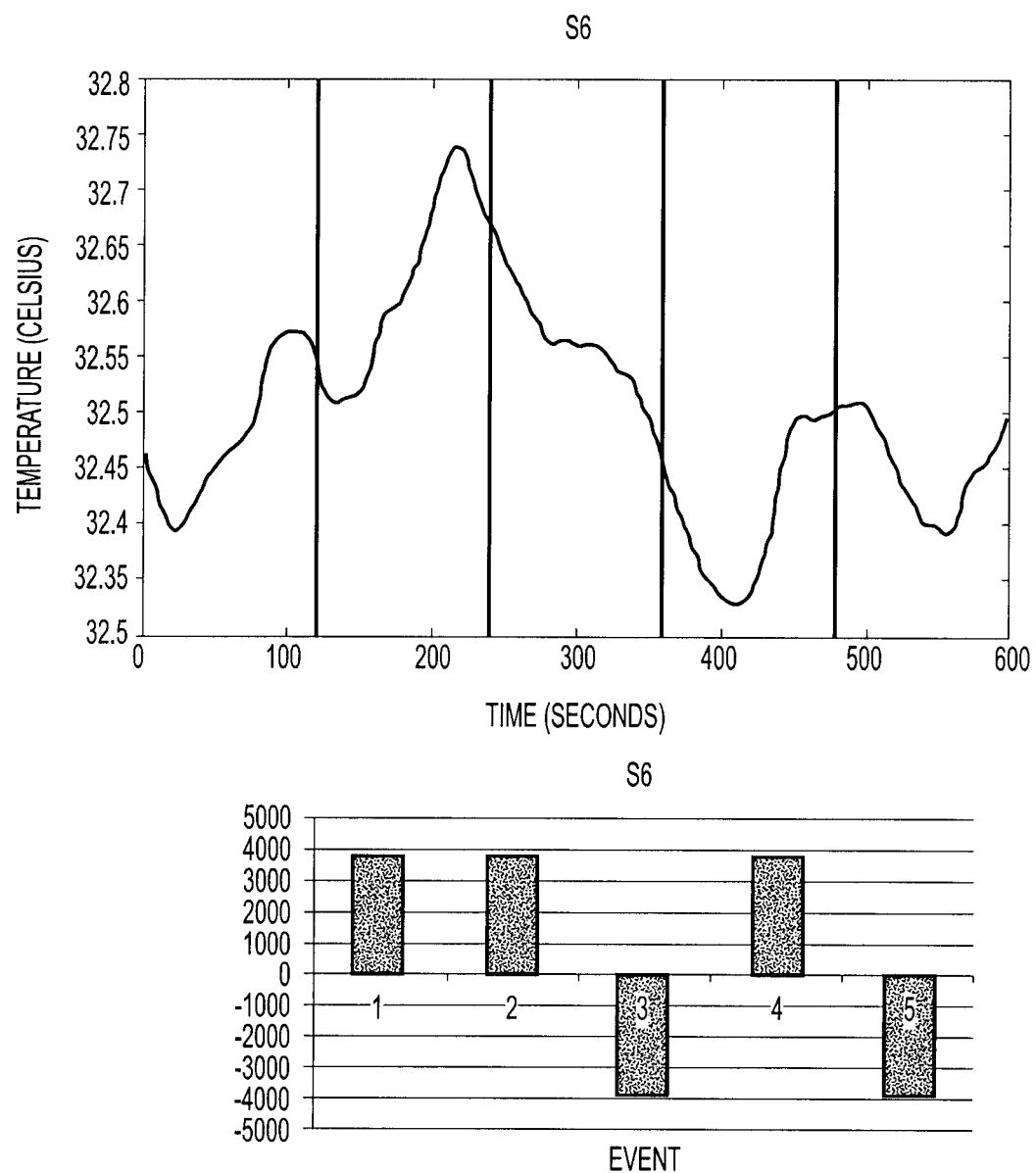

A practical realization of the above described system 100 and method has been implemented and is described herein below. FIG. 18 is a perspective view of a realization of a neurotuner according to an embodiment. A system 200 comprises a main control unit 210 that generally incorporates most elements of the system 100 of FIG. 2. The main control unit 210 comprises a source of a facilitation signal and a source of an excitatory signal, with separate signal controls 212 and 214. The system 200 also comprises a facilitation signal interface 216 connected to an audio headset 218 and an excitatory signal interface 220 connected to a tactile signal activator 222. The tactile signal activator 222 may also function as a temperature sensor or the temperature can be measured independently using a temperature sensor 224 connected to the main control unit 210 via a physiological response interface 226. Finally, the system 200 comprises an operator interface 228 for automatically controlling the main control unit 210.

The system 200 uses a computer interface comprising a transducer loop 140, and a channel loop 142 that measure the evolution of the subject's peripheral temperature which, in this particular example, represents the excitatory signal. This computer interface is based on the fact that a subject's body peripheral temperature as measured on its extremities varies according to the amount of blood perfusing the skin. This, in turn, is dependent on the client's state of sympathetic arousal. As a person gets stressed, their fingers tend to get colder. This phenomenon is well known in the field of relaxation training, in which subjects learn to voluntary increase the finger temperature. Herein the sub-threshold level represents a stress state.

A similar exercise was performed with six (6) subjects. The subjects were not asked to learn to voluntarily increase their finger temperature. Instead, finger temperature increases were facilitated by using an effective auditory randomly determined signal. Subjects began the experiments with a no facilitation signal condition during two (2) minutes, and then three randomly determined signal levels, ranging from low, medium and high amplitude, were applied to the audio headsets 218 during periods of two (2) minutes each. Finally, a no facilitation condition was applied again for another period of two (2) minutes. The tactile signal activator 222 was strapped to the palmar side of the index finger using a short strip of Velcro in order to obtain a reading of their finger temperature. FIGS. 19-24 provide experimental results obtained using the neurotuner of FIG. 18. These Figures were obtained from six (6) subjects represented as S1-S6. In each of the FIGS. 19-24, an upper part shows a graph of index finger palmar side temperature over time, the graphs being split into the following five (5) consecutive conditions: (a) no facilitation signal, (b) low randomly determined level, (c) medium randomly determined level, (d) high randomly determined level, and (e) no facilitation signal. The lower part of the Figures shows histograms of an optimal index—described herein below—in relation with the auditory conditions (a-e) of the facilitation randomly determined signal.

The following observations may be made from the experimental results:
1) In subjects S1, S2, S3, S4, S5 the temperature decreased, in average, in the first no facilitation signal condition.
2) Generally, one of the randomly determined levels was more effective to increase the temperature in all the participants.
3) In subjects S1, S3, S4, S6 the temperature decreased, on average, in the last no facilitation signal condition.
4) Only in subjects S2 and S5 the temperature increased, on average, in the no facilitation signal condition,
5) In general the auditory randomly determined signal was effective for increasing the temperature.

The point of maximum sensation was measured as follows: Experiments began with a no facilitation condition during two (2) minutes. The interface took measurements of temperature changes. Application of an auditory randomly determined signal was manually initiated, at low amplitude level. Observation was made of whether the temperature increased, in which case this level was maintained until the temperature began to decrease. The level of the facilitation signal was raised again, to a medium amplitude level. The process was repeated when the randomly determined signal amplitude level was high, which was a predetermined maximum for the experiment. In most subjects, the temperature would decrease while this high amplitude randomly determined signal was present. The operator interface 228 then calculated an integral providing a surface under the curves at the top of FIGS. 19-24. The operator interface 228 also calculated an average gradient normalized by its own magnitude. Of course, this consistently provided a unitary value that either positive or negative, depending on a positive or negative slope of the curves. A product of the area under the curve and the positive or negative unit designated an optimal facilitation signal level, also referred herein as optimal index. The optimal facilitation level was thus the one with the highest positive optimal index. The operator interface 228 may automatically determine which facilitation level provides the optimal index, but this determination may of course be done manually based on the experimental results.

In a variant, an adaptive loop can be implemented; the operator interface 228 may also apply automatically the required auditory facilitation signal to find the optimal index. The operator interface 228 may calculate the temperature gradient in real time. If the gradient is positive or zero the auditory facilitation amplitude is not changed. Otherwise, the auditory facilitation signal is incremented until the gradient is again zero or positive. It has been observed that a waiting time of two (2) minutes before the operator interface 228 increased the auditory facilitation level was satisfactory. If the gradient remains negative after two noise level increments, the operator interface 228 may be configured to stop the process and determine automatically the optimal index as in paragraph the above paragraph.

The present disclosure has been described in the foregoing specification by means of non-restrictive illustrative embodiments provided as examples. These illustrative embodiments may be modified at will. The scope of the claims should not be limited by the embodiments set forth in the examples, but should be given the broadest interpretation consistent with the description as a whole.

What is claimed is:

1. A system for evaluating stimulus sensitivity of a subject, comprising:
   a first action channel configured to provide a first type stimulus to the subject;
   a reaction channel configured to receive a response from the subject, wherein the action and reaction channels are implemented by means of actuators and sensors;
   a signal pathway connected to the first action channel and to the reaction channel; and
   a controller adapted to establish at least one of:
      a first transduction loop including the first action channel and forming a path terminating in the signal pathway,
      a first channel loop including the first action channel forming a path through the signal pathway and terminating at a first reference unit,
      an interface loop including the first action channel, the reaction channel and the first reference unit, the first reference unit having a first initial parameter value; and
      an adaptive loop including the first action channel, the reaction channel and the first reference unit, the first reference unit being adjusted from the first initial parameter value to a first adapted parameter value based on the response from the subject;
   wherein the signal pathway is an automatically configurable signal pathway formed of switches that open and close per commands from the controller allowing for dynamically reconfiguring the system so that an action channel may become a reaction channel according to a pre-established program or to the subject responses in real or delayed time.

2. A system as defined in claim 1, comprising a plurality of action channels.

3. A system as defined in claim 1, comprising a plurality of reaction channels.

4. A system as defined in claim 1, wherein the signal pathway extends from a main control unit including the controller to connect the main control unit to the first action channel and to the reaction channel.

5. A system as defined in claim 1, comprising a second action channel configured to provide a second type stimulus to the subject and connected to the signal pathway.

6. A system as defined in claim 5, wherein the controller is further adapted to establish:
   a second transduction loop including the second action channel and a second relay unit of the signal pathway, a second channel loop including the second action channel and a second reference unit of the controller, and a mixed loop including the first action channel, the second action channel, the first reference unit and the second reference unit;
   wherein the interface loop further includes the second action channel and the second reference unit, the second reference unit having a second initial parameter value; and
   wherein the adaptive loop further includes the second action channel and the second reference unit, the second reference unit being adjusted from the second initial parameter value to a second adapted parameter value based on the response from the subject.

7. A method for evaluating stimulus sensitivity of a subject using the system of claim 6, comprising:
   using the first action channel as a source of an excitatory signal to stimulate a first sensory, reflex and/or motor mechanism of the subject;
   using the second action channel as a source of a facilitation signal to stimulate a second sensory, reflex and/or motor mechanism of the subject; and
   measuring, using the reaction channel, a physiological response of the first sensory, reflex and/or motor mechanism.

8. A method as defined in claim 7, comprising:
   adjusting a level of the facilitation signal based on the measured physiological response;
   wherein adjusting the level of the facilitation signal improves the sensitivity of the first sensory, reflex and/or motor mechanism due to the Fulcrum Principle interactions;
   whereby sensitivity of the first sensory, reflex and/or motor mechanism of the subject is improved.

9. A method as defined in claim 7, wherein the facilitation signal is a deterministic or randomly determined signal.

10. A method as defined in claim 7, wherein stimulating the second sensory, reflex and/or motor mechanism comprises an element selected from the group consisting of applying an auditory signal to at least one ear of the subject, applying a visual signal to at least one eye of the subject, applying a tactile signal to at least one part of the subject's body, applying an electromagnetic signal to at least one area of the subject's body, applying a thermal signal to at least one area of the subject's body, applying a vibratory signal to at least one area of the subject's body, providing for the subject to detect an odor and providing for the subject to taste a gustatory sample.

11. A system for improving sensitivity of a first sensory, reflex and/or motor mechanism of a subject, comprising:
   a source of a facilitation signal for stimulating a second sensory, reflex and/or motor mechanism of the subject;
   a sensor for measuring a physiological response of the first sensory, reflex and/or motor mechanism; and
   a controller providing for automatically selecting the source of the facilitation signal and automatically adjusting a level of the facilitation signal based on the measured physiological response and the evolution of the measured physiological response over a plurality of measurements;

wherein adjusting the level of the facilitation signal improves the sensitivity of the first sensory, reflex and/or motor mechanism of a subject due to Fulcrum Principle interactions;

wherein the controller is configured to:
a) first apply no facilitation signal;
b) acquire a first physiological response measurement while there is no facilitation signal;
c) increase a level of the facilitation signal;
d) acquire a next physiological response measurement;
e) detect an inflexion point of the next physiological response measurement;
f) following detection of the inflexion point, repeat the processes c), d) and e) until a predetermined maximum level of the facilitation signal is reached; and
g) adjust the level of the facilitation signal by selection of a level of the facilitation signal providing a maximum physiological response that is increasing over a duration of acquisition thereof.

12. A system as defined in claim 11 wherein the source of the facilitation signal is selected from the group consisting of a visual stimulation device, a vibratory stimulation device, an electromagnetic stimulation device, a thermal stimulation device, a tactile stimulation device, an acoustic stimulation device, a source of an odor placed within a short distance of the subject, and a device providing a gustatory sample for tasting by the subject.

13. A system as defined in claim 11, wherein the source of the facilitation signal is configured to apply a direct stimulation to a particular area of the subject's body.

14. A system as defined claim 11, comprising two sources for applying a differential facilitation signal by stimulating two different areas of the subject's body in order to stimulate a region of the subject's body between the two different areas.

15. A system as defined in claim 11, comprising a plurality of sources for applying a distributed facilitation signal by stimulating several areas of the subject's body in order to stimulate a region of the subject's body covered by the several areas.

16. A system as defined in claim 11, comprising a plurality of sources of different types for applying a plurality of different facilitation signals to the patient's body.

17. A system as defined in claim 11, further comprising an interface for connecting the system to a computer for transferring thereto information about a stimulation process.

18. A system as defined in claim 11, wherein the sensor is configured to measure a temperature at the first sensory, reflex and/or motor mechanism.

19. A system as defined in claim 11, wherein the controller is configured to perform each physiological measurement acquisition in real time.

20. A system as defined in claim 11, wherein the selection of a level of the facilitation signal providing a maximum physiological response that is increasing over a duration of acquisition thereof comprises:
a calculation of an integral of each physiological response measurement over its duration of acquisition;
a calculation of a gradient of each physiological response, wherein the gradient is normalized by its own magnitude;
a calculation of for each physiological response a product of the integral with its gradient; and
a selection of a highest positive product.

21. A system as defined in claim 11, comprising:
a source of an excitatory signal for stimulating the first sensory, reflex and/or motor mechanism;
wherein the controller is configured to, before adjusting the level of the facilitation signal, adjust a level of the excitatory signal to sub-threshold level at the first sensory, reflex and/or motor mechanism.

22. A system as defined in claim 21, wherein the controller is configured to adjust the level of the excitatory signal to sub-threshold level at the first sensory, reflex and/or motor mechanism by reducing the level of the excitatory signal until it is no longer detectable by the subject.

23. A system as defined in claim 21, wherein the source of the excitatory signal is selected from the group consisting of a visual stimulation device, a vibratory stimulation device, an electromagnetic stimulation device, a thermal stimulation device, a tactile stimulation device, an acoustic stimulation device, a source of an odor placed within a short distance of the subject, and a device providing a gustatory sample for tasting by the subject.

24. A system as defined in claim 21, comprising:
a stimulator connected to the source of the excitatory signal for applying the excitatory signal to the first sensory, reflex and/or motor mechanism; and
another stimulator connected to the source of the facilitation signal for applying the facilitation signal to the second sensory, reflex and/or motor mechanism.

* * * * *